United States Patent [19]

Hart et al.

[11] Patent Number: 5,782,839
[45] Date of Patent: Jul. 21, 1998

[54] LAPAROSCOPIC SURGICAL GRASPER HAVING A DETACHABLE STRAP

[75] Inventors: Colin P. Hart, Clarence Center; Norbert W. Frenz, Jr., Williamsville; Richard M. Garlapow, Grand Island; Robert C. Jackson, Clarence; Thomas W. Klementowski, Amherst; Jack A. Belstadt, Lockport, all of N.Y.

[73] Assignee: Wilson Greatbatch Ltd., Clarence, N.Y.

[21] Appl. No.: 546,304

[22] Filed: Oct. 20, 1995

Related U.S. Application Data

[63] Continuation-in-part of Ser. No. 402,344, Mar. 10, 1995, Pat. No. 5,613,973.

[51] Int. Cl.$^6$ ............................................. A61B 17/24
[52] U.S. Cl. ...................... 606/113; 606/110; 606/127; 606/198
[58] Field of Search ........................ 606/127, 198, 606/110, 113, 114, 1; 604/93

[56] References Cited

U.S. PATENT DOCUMENTS

| | | | |
|---|---|---|---|
| 480,870 | 8/1892 | Harris . | |
| 668,647 | 2/1901 | Jaenicke . | |
| 1,461,864 | 7/1923 | Day . | |
| 1,470,914 | 10/1923 | Day . | |
| 2,054,149 | 3/1936 | Wappler | 128/309 |
| 3,181,533 | 5/1965 | Heath | 128/320 |
| 3,791,387 | 2/1974 | Itoh | 606/113 |
| 3,828,790 | 8/1974 | Curtiss et al. | 128/320 |
| 3,903,892 | 9/1975 | Komiya | 606/110 |
| 4,046,149 | 9/1977 | Komiya | 606/127 |
| 4,592,355 | 6/1986 | Antebi | 606/144 |
| 4,691,705 | 9/1987 | Okada | 606/127 |
| 5,084,054 | 1/1992 | Bencini et al. | 606/113 |
| 5,106,369 | 4/1992 | Christmas | 604/51 |
| 5,108,406 | 4/1992 | Lee | 606/106 |
| 5,152,771 | 10/1992 | Sabbaghian et al. | 606/198 |
| 5,163,942 | 11/1992 | Rydell | 606/113 |
| 5,320,629 | 6/1994 | Noda et al. | 606/113 |
| 5,417,684 | 5/1995 | Jackson et al. | 606/1 |
| 5,441,044 | 8/1995 | Tovey et al. | 606/198 |
| 5,613,973 | 3/1997 | Jackson et al. | 606/113 |

*Primary Examiner*—Robert A. Hafer
*Assistant Examiner*—Justine R. Yu
*Attorney, Agent, or Firm*—Hodgson, Russ, Andrews, Woods & Goodyear LLP

[57] ABSTRACT

A medical grasper device (10) that is useful for grasping and manipulating a body organ is described. The grasper device is partially inserted into a body cavity and comprises a flexible strap (16) having a distal section (18) that is deployed from a tube (12) to form a partially closed loop (22). A terminal end of the strap has an attachment means, such as aperture (32), that is manipulated by a separate forceps-type device to mate the attachment aperture with a connection means (34) to complete the loop. The closed loop is then adjustable in size to provide for positioning the loop at a desired location around the target body organ to grasp and manipulate the body organ. Various embodiments show the connection means provided on either the tube, a drive rod (406) disposed in a movable relationship inside the tube and on the strap itself, and connectable to the strap attachment means to close the loop.

9 Claims, 15 Drawing Sheets

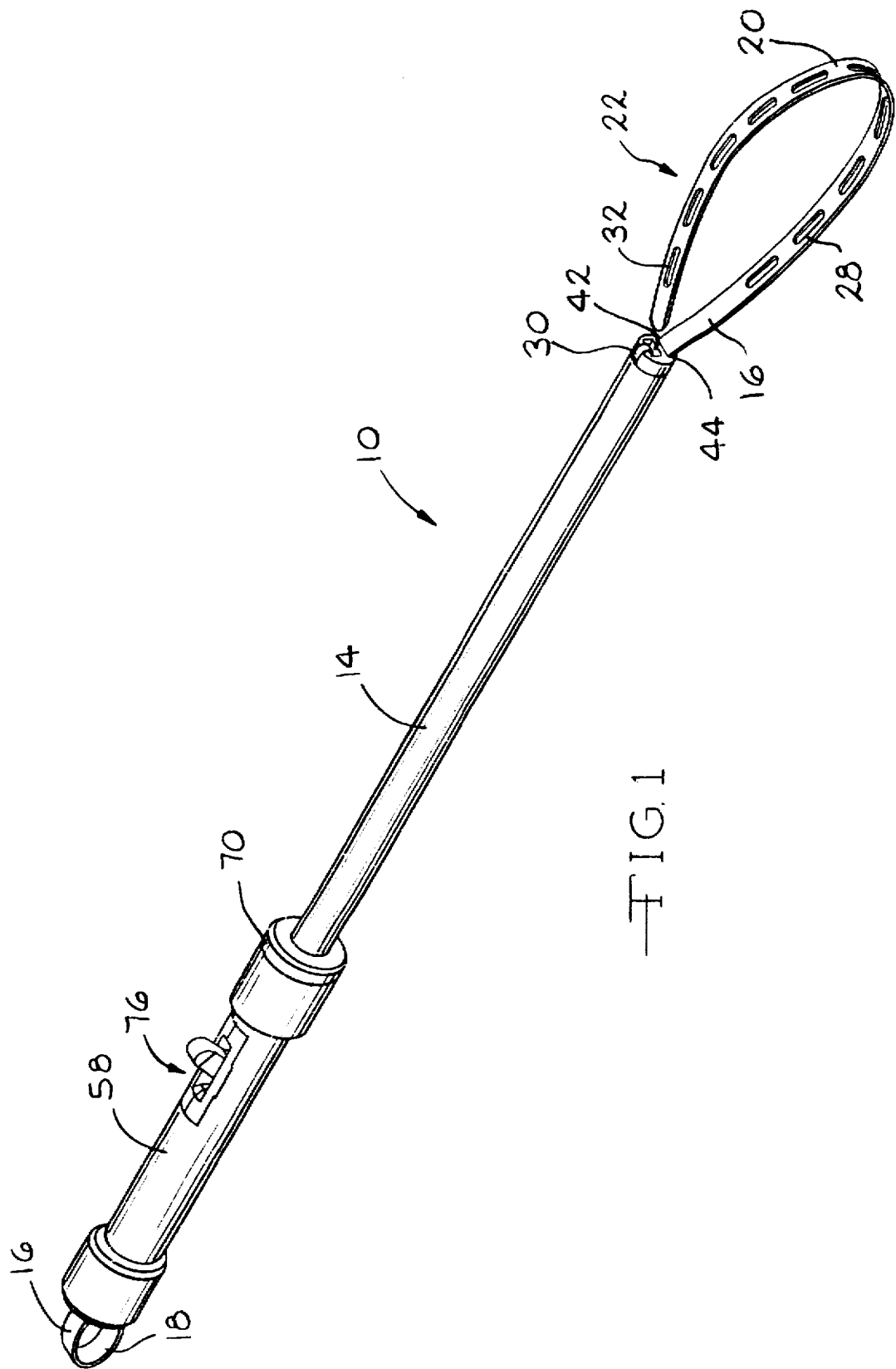

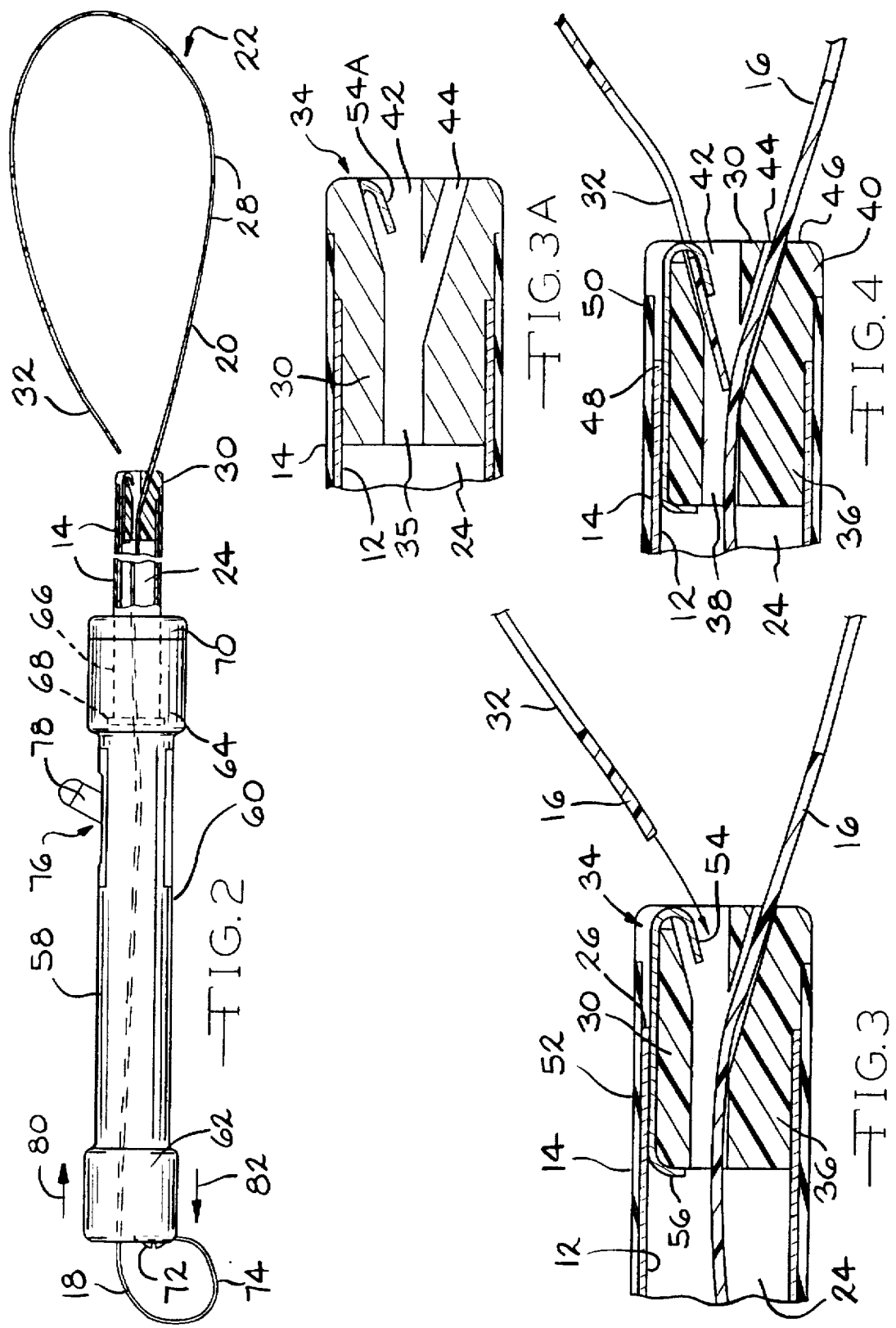

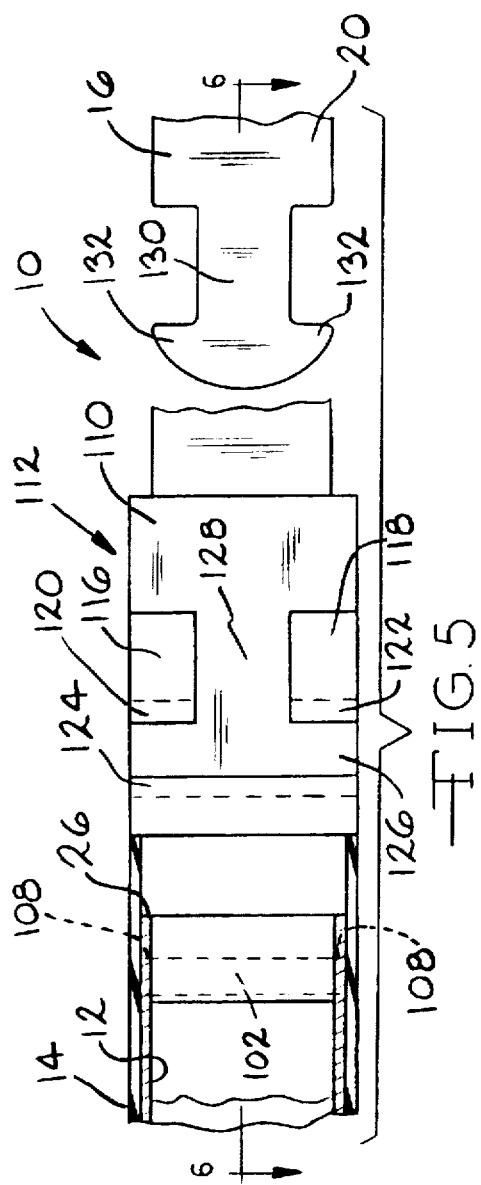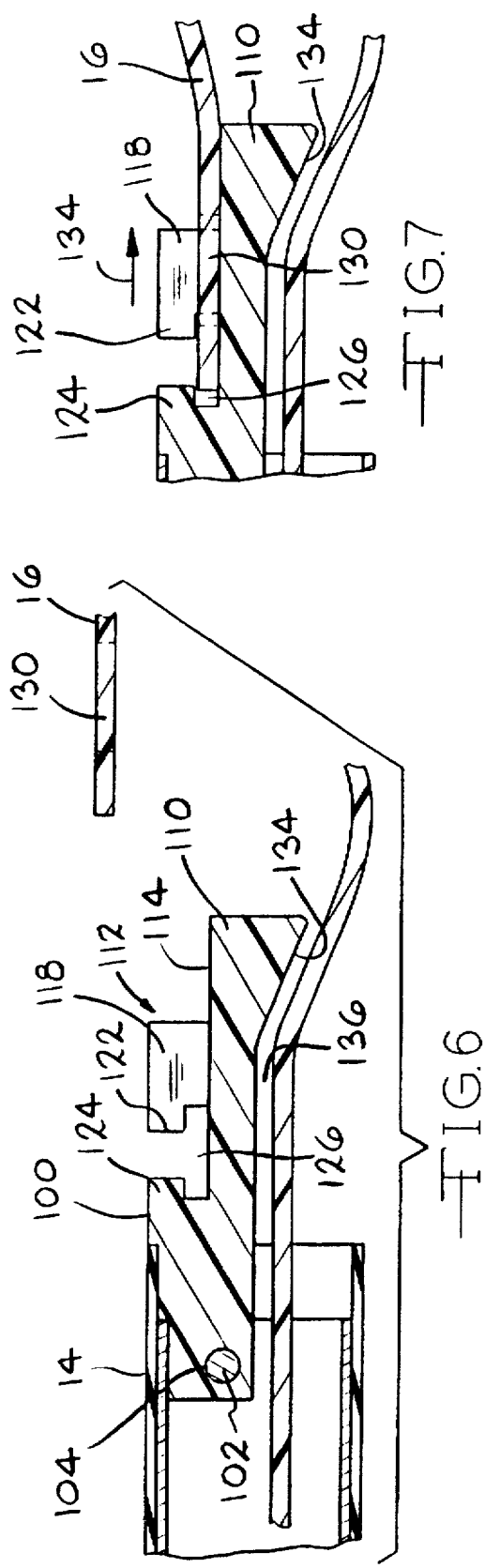

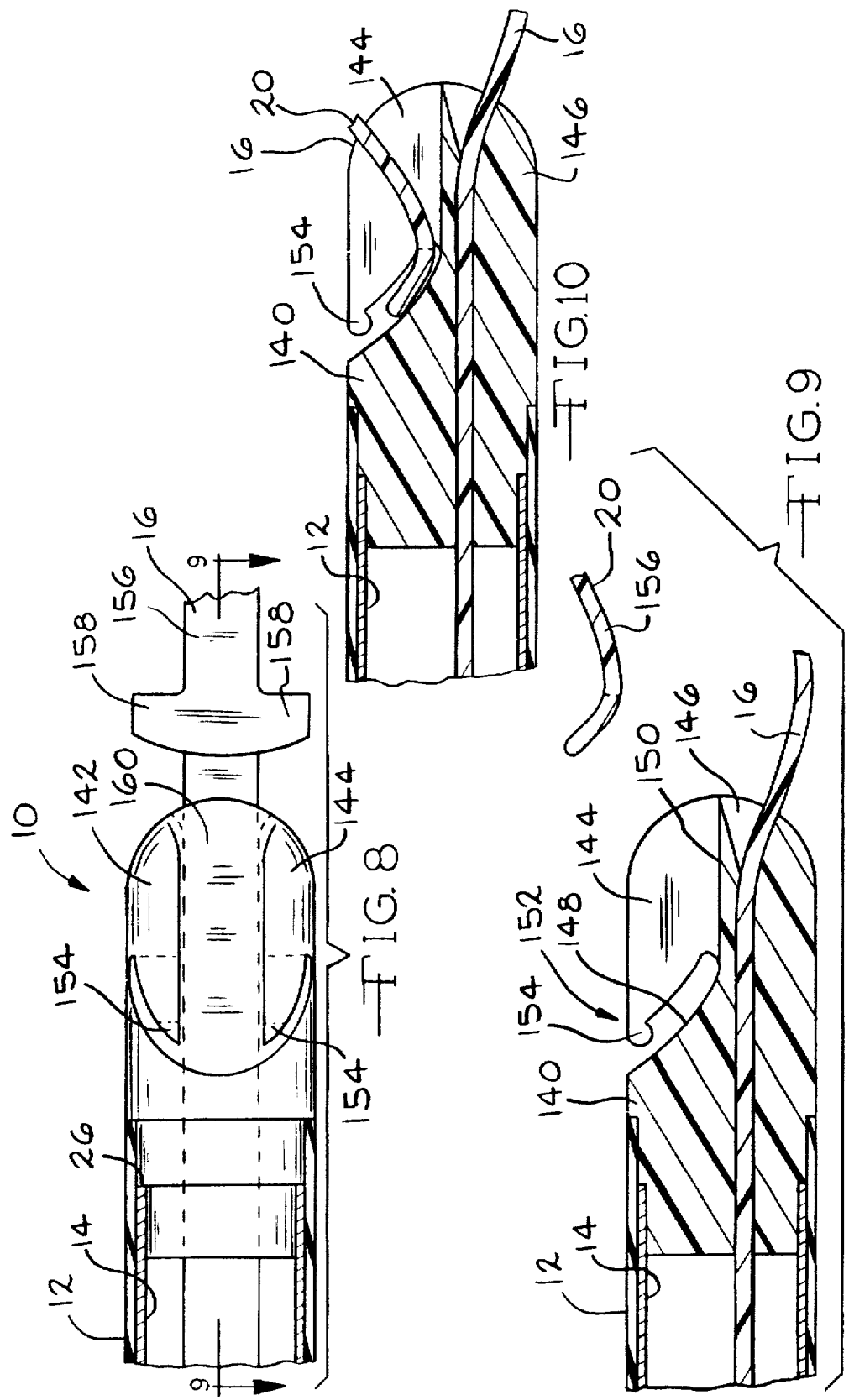

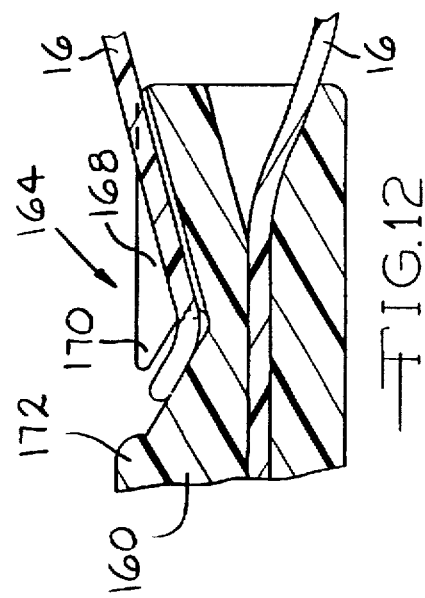
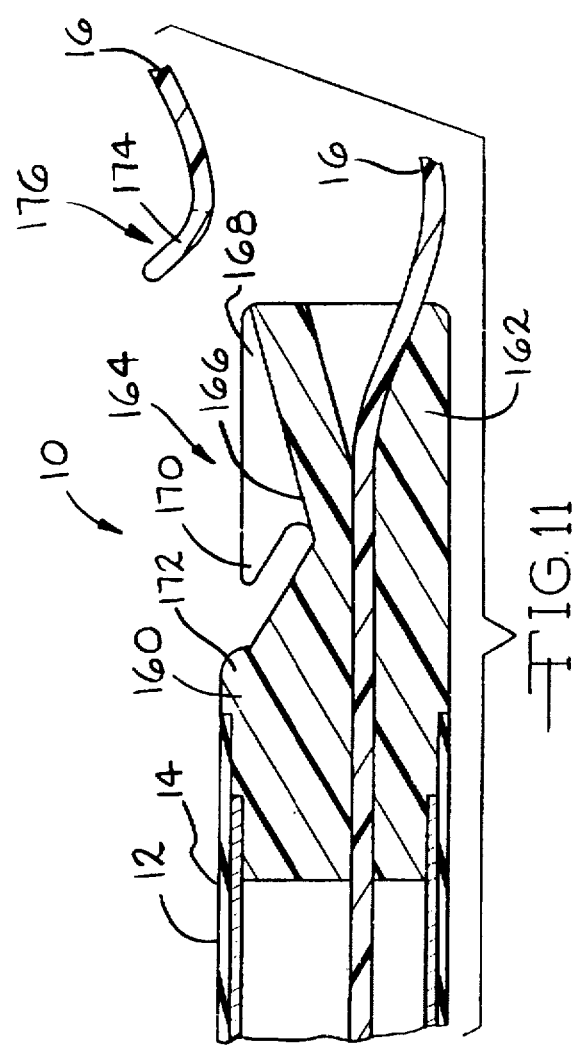

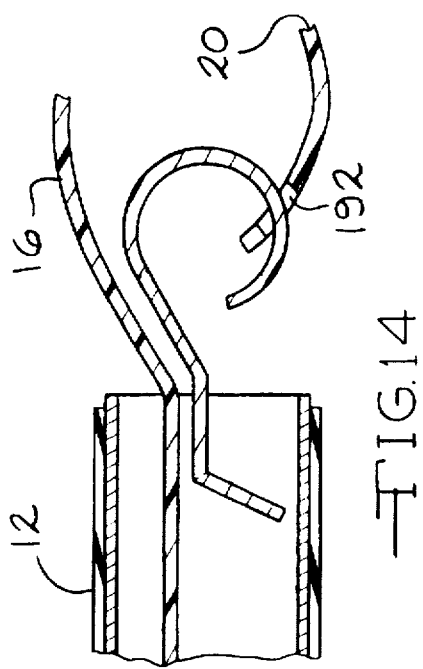
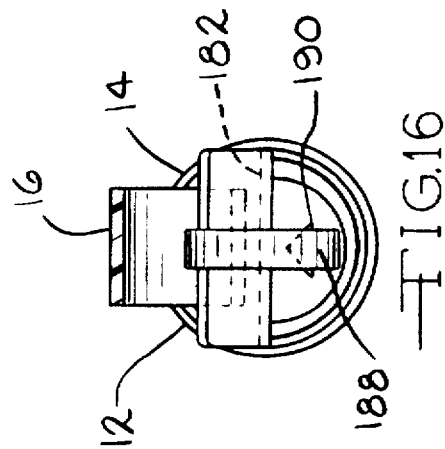
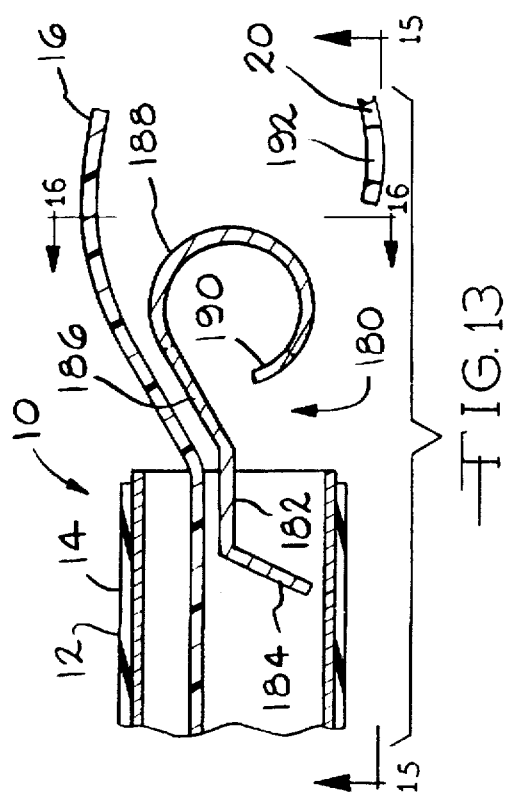
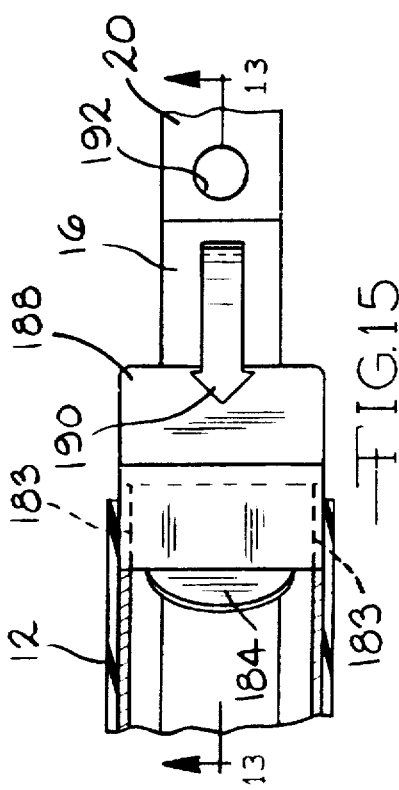

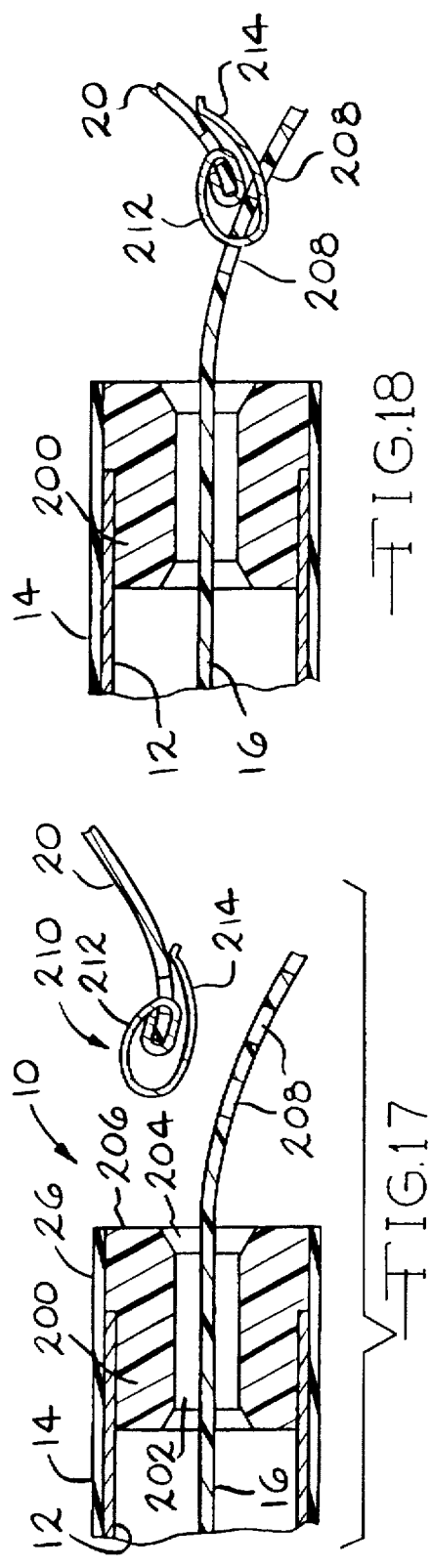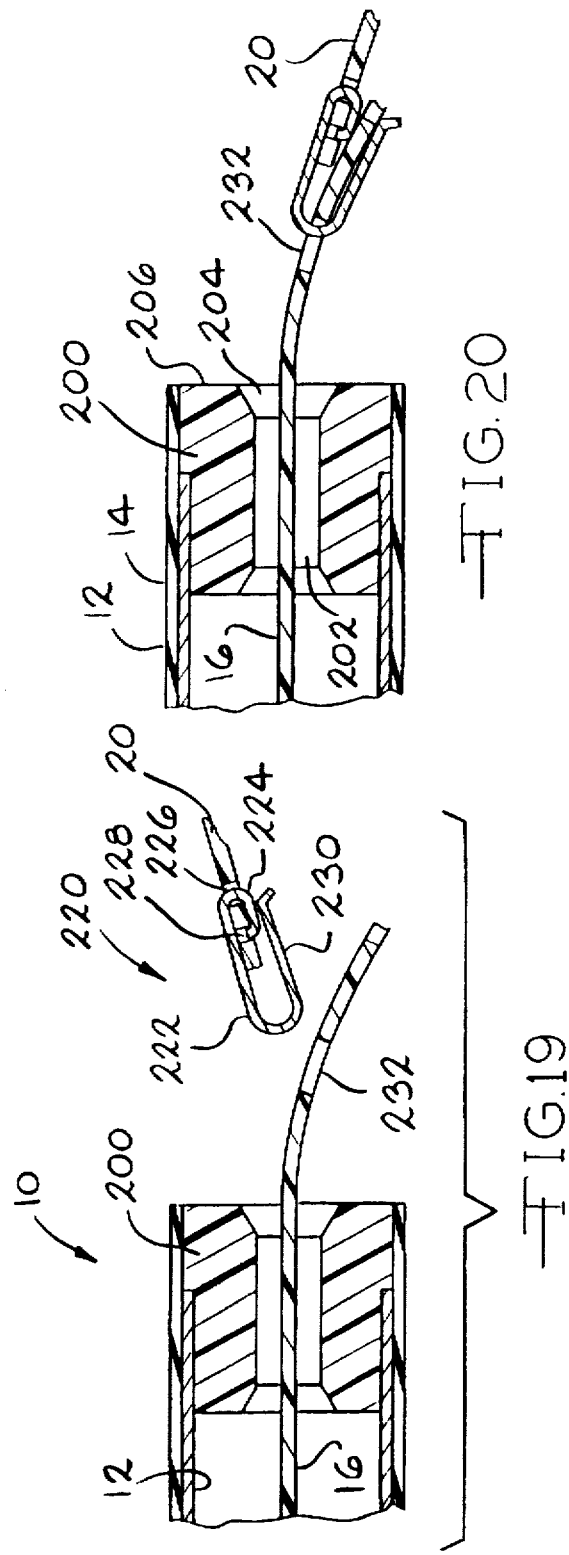

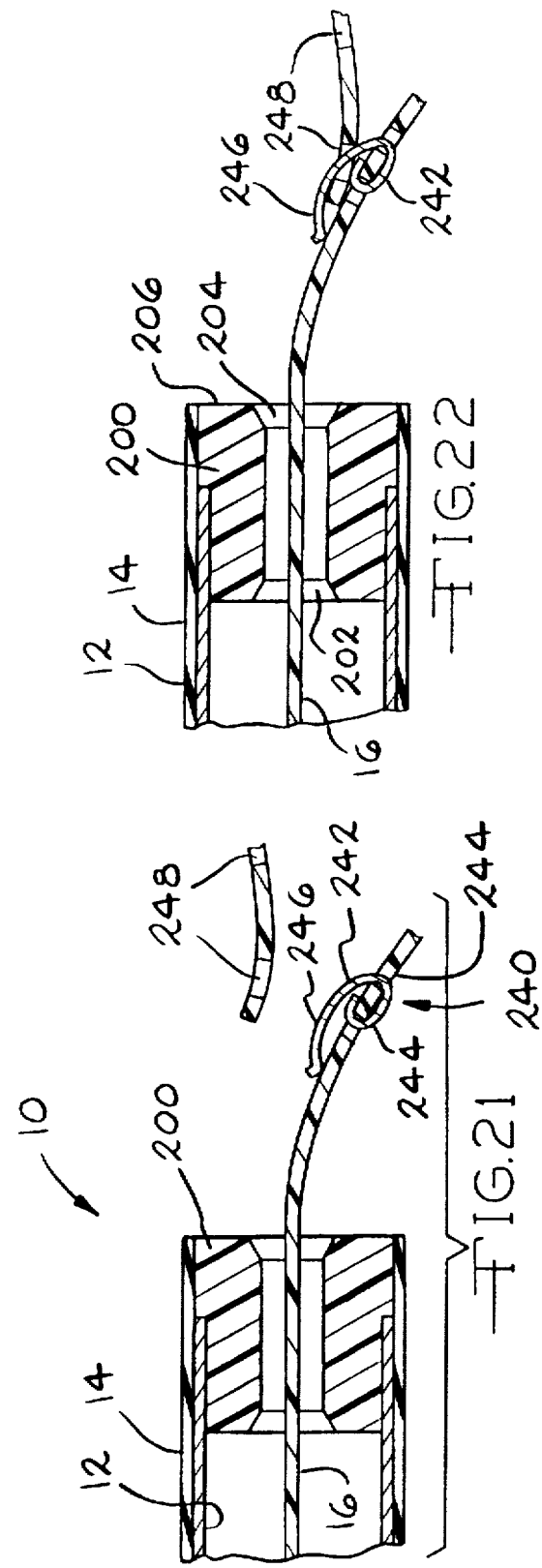

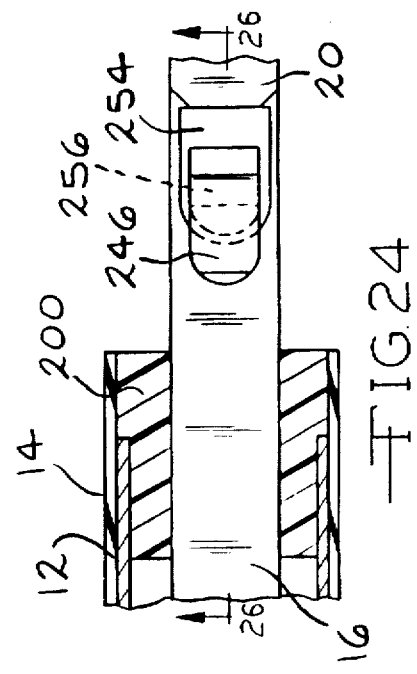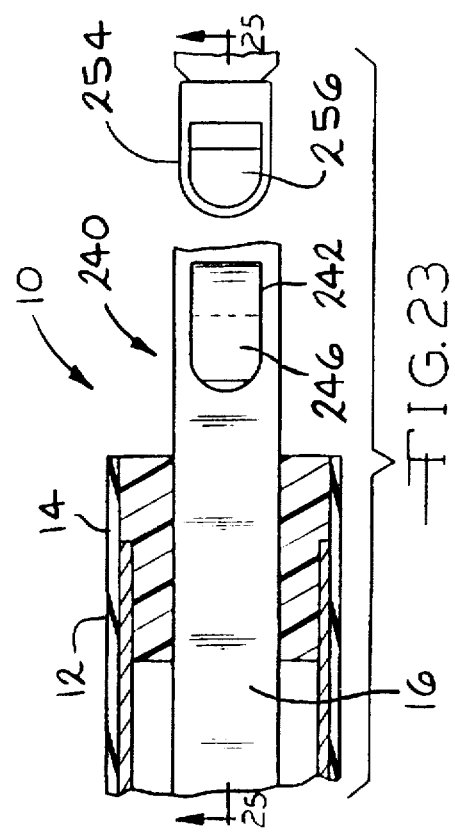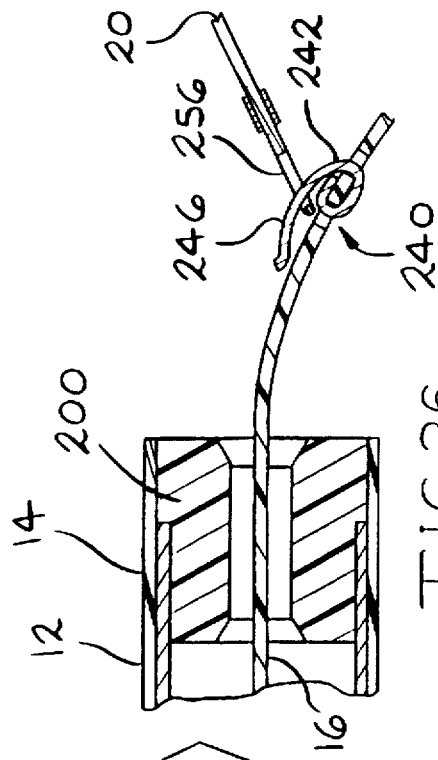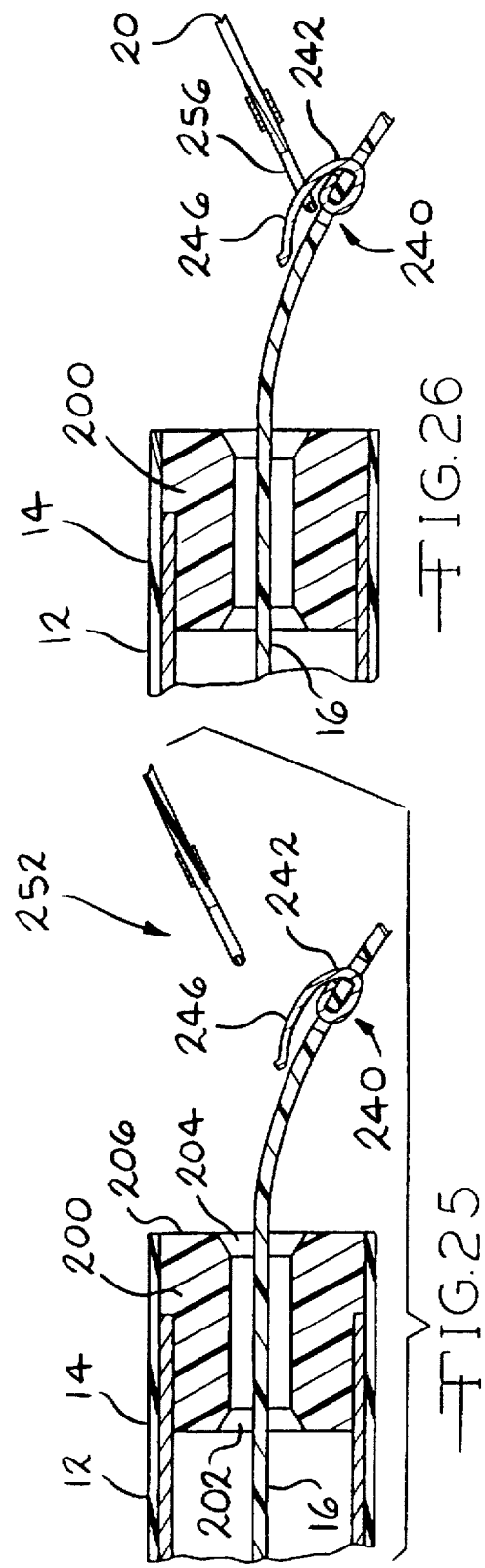

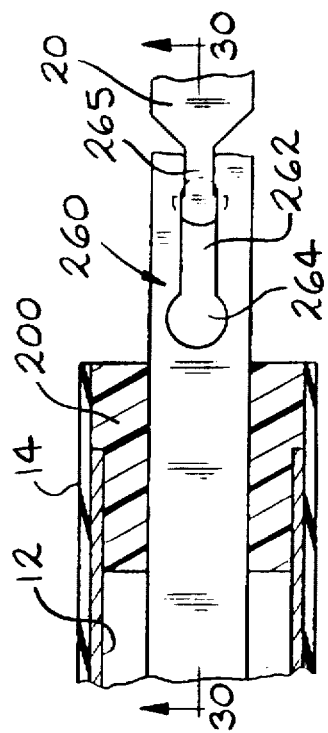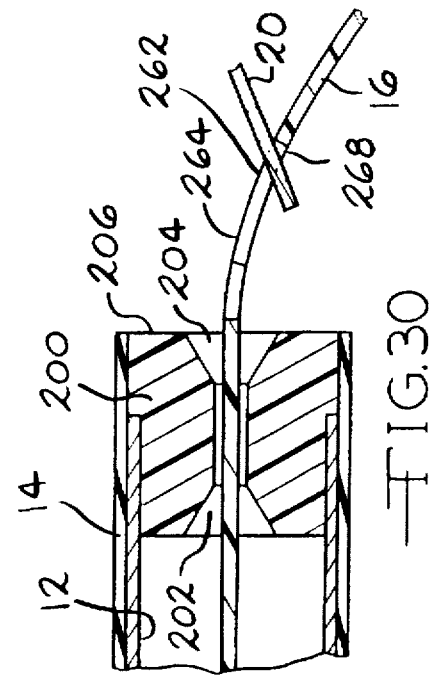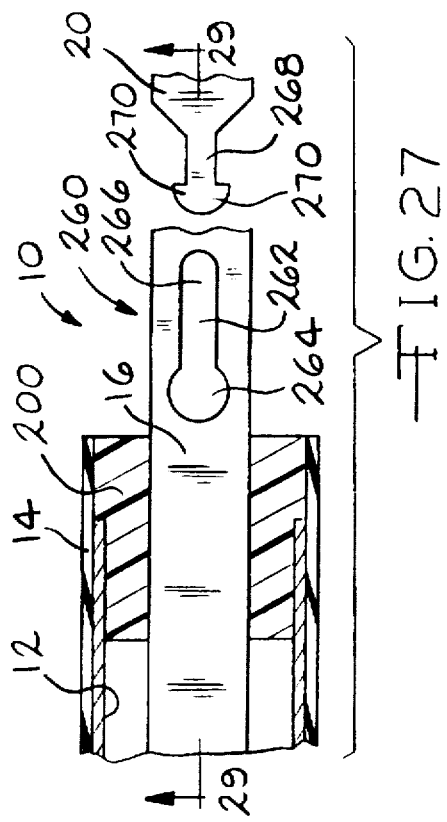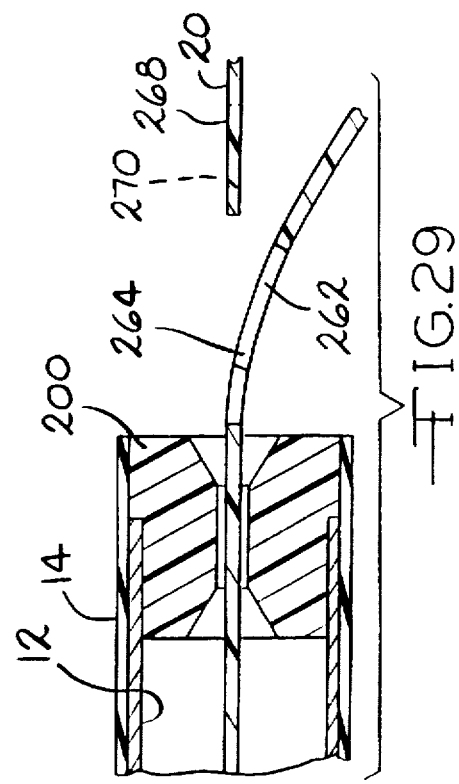

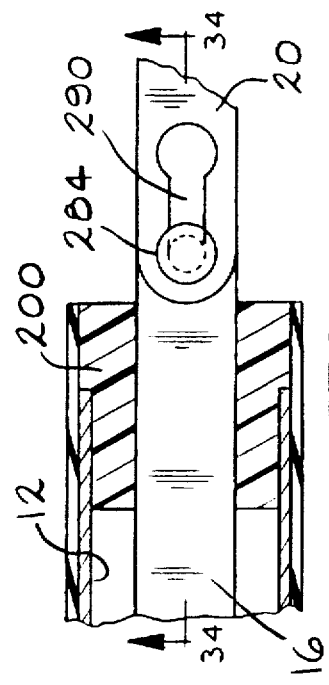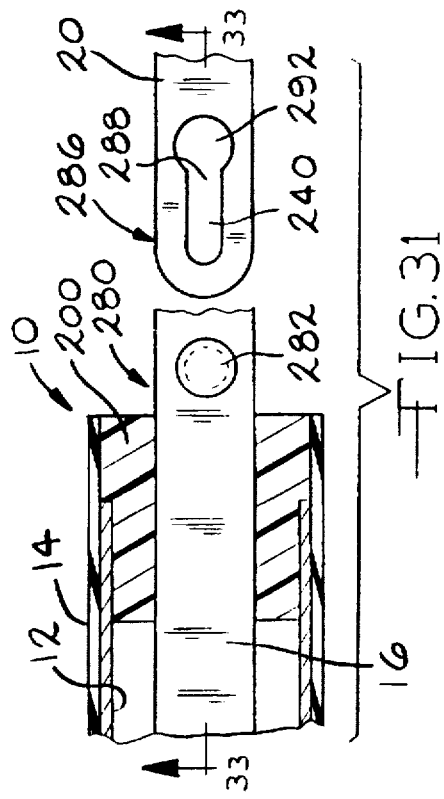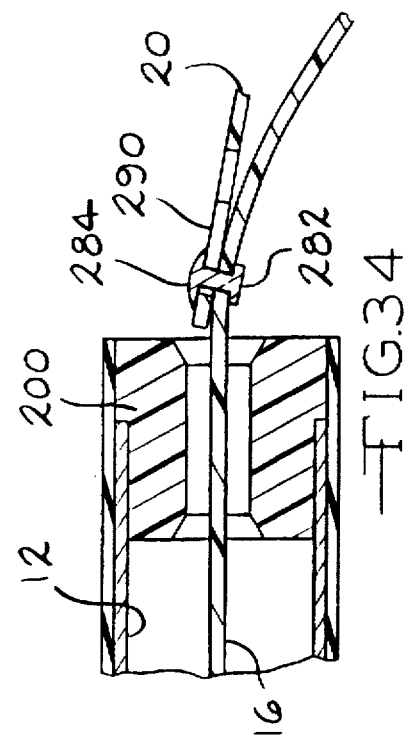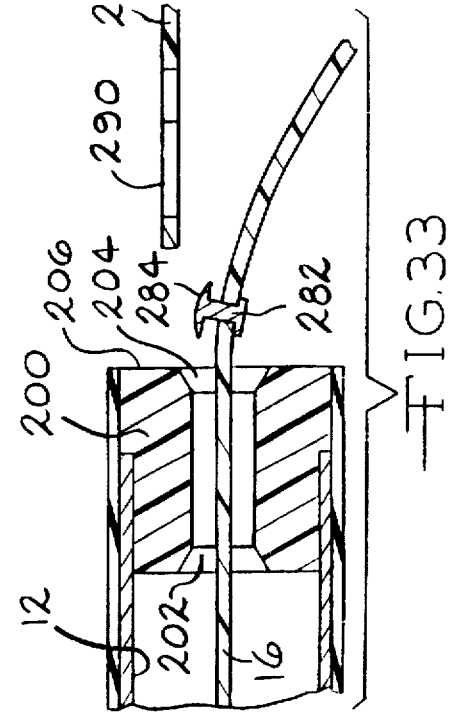

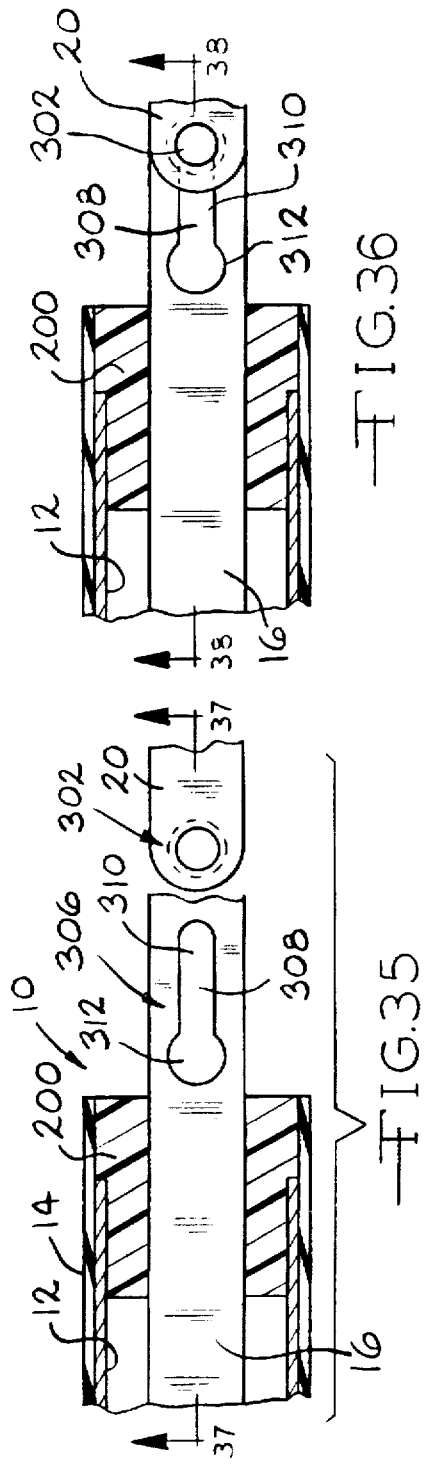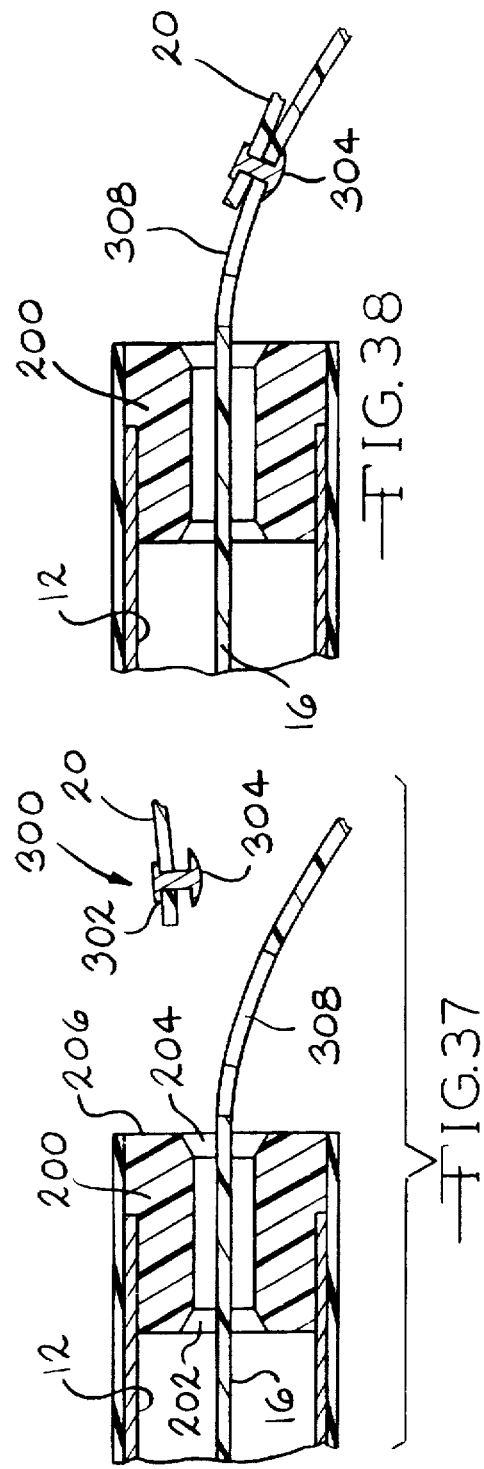

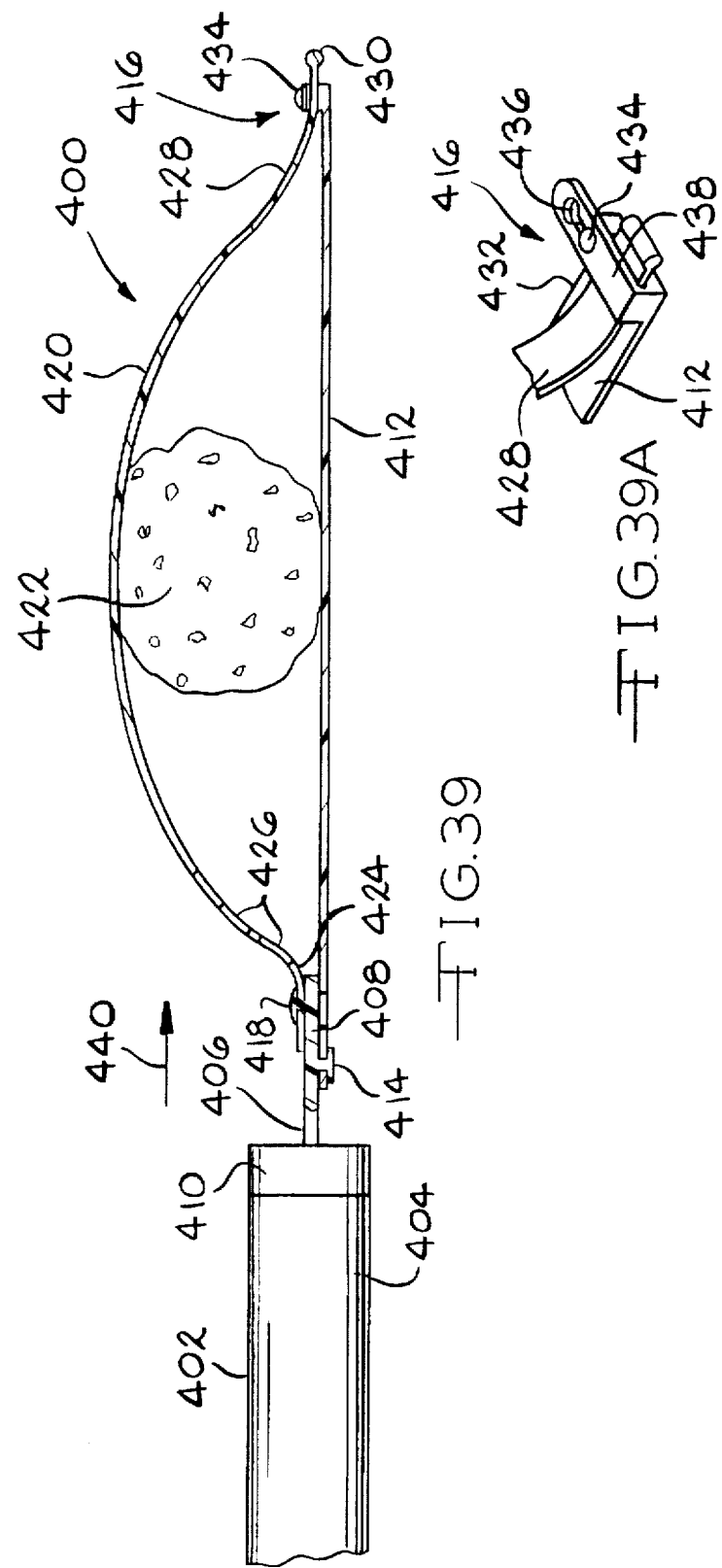

5,782,839

1

LAPAROSCOPIC SURGICAL GRASPER HAVING A DETACHABLE STRAP

CROSS-REFERENCE TO RELATED APPLICATION

This application is a continuation-in-part of application Ser. No. 08/402,344, filed Mar. 10, 1995, now U.S. Pat. No. 5,613,973 to Jackson et al.

BACKGROUND OF THE INVENTION

1. Field of the Invention

The present invention generally relates to a medical device and, more particularly, to a grasper device that is useful for grasping and manipulating a body organ during a laparoscopic surgical procedure. More specifically, the grasper device of the present invention has a manipulative means and a strap that is manipulatable around a body organ, particularly the type of organ that is connected to adjoining tissue at both ends, such as the colon. The strap is then attachable to and detachable from a strap connection means provided either on the conduit means or the manipulative means to encircle the body organ. This enables a surgeon to move the body organ as needed during the laparoscopic surgical procedure.

Given the current trend to reducing patient trauma as much as possible by performing operative procedures that are less invasive and less traumatic to the patient and the subject body organ, laparoscopic surgical procedures are being performed with increasing frequency. Laparoscopic surgery is a form of abdominal surgery using a laparoscope and other surgical instruments introduced into the abdomen through separate cannula ports. A laparoscope is an instrument for visualizing the interior of the abdomen and the various body organs contained therein. In laparoscopic surgery, the laparoscope is introduced into a body cavity, such as the abdomen, through a cannula port fitted to a trocar, which is a sharp pointed instrument that is punctured through the body cavity wall to insert the cannula. The grasper device of the present invention is introduced into the body cavity through a separate cannula port where it is used to grasp and manipulate a body organ and/or body tissue attached to adjoining body tissue at both ends during the surgery in a non-slip and a traumatic engagement. Additional cannula ports are used for other surgical instruments needed for the surgical procedure.

2. Prior Art

The advent of laparoscopic surgery has fostered the rapid development of improved surgical methods and concomitant advancements in instruments that are useful to a surgeon performing the surgery.

U.S. Pat. No. 5,417,684 to Jackson et al., which is assigned to the assignee of the present invention and incorporated herein by reference, describes a medical grasper device including a flexible strap having traction formations that serve to prevent the strap from releasing from a position encircling a body organ. During the laparoscopic procedure, the strap is moved out through the distal end of a tube to define a loop of adjustable size that is useful for grasping and manipulating the body organ. However, the strap forming the loop is not attachable and detachable to a strap connection means and therefore, is not particularly suitable for use with body organs of the type that are connected to adjoining tissue at both ends.

U.S. Pat. No. 4,592,355 to Antebi describes an instrument that is useful for tying live tissue. This instrument comprises a flexible strap that is looped around the body tissue and inserted into a head member. Teeth on the strap engage a pawl in the head to prevent the loop from opening. This strap is particularly useful for ligating hemorrhoidal tissue because once the strap is tightened, it is not intended to be loosened.

The prior art also has described numerous snare devices having narrow width belts or wires that are useful for holding a body organ, cutting tissue and removing malignant growths. Representative of these devices are U.S. Pat. Nos. 480,870; 668,647; 1,461,864; 1,470,914; 2,054,149; 3,181,533; 3,828,790; 5,084,054 and 5,163,942.

What is therefore needed is a grasper device having a strap means housed inside a tube serving as a conduit means for the strap wherein the strap is attachable to and detachable from a connection means provided on either the conduit means, a manipulative means housed therein or, the strap itself to form a grasping loop. Such an attachable and detachable strap is useful for encircling a body organ, such as a colon or umbilical cord, that is connected to adjoining body tissue at both ends. Thus, a terminal end of the strap is provided with an attachment means that is manipulated by a forceps-type device to attach the strap means to the connection means to close the loop around the body organ. The closed loop and associated grasper device is then useful for grasping and manipulating the body organ. The attachment means further provides for detaching the strap from the connection means to reposition the loop or for withdrawing the grasper device from the body cavity. The strap can further be provided with memory-curved characteristics that provide the strap defining a partially closed loop upon deployment from the conduit means.

In that respect, the strap needs to be flexible to provide for adjusting the size of the loop, but have relative rigidity in a plane normal to the loop to provide maneuverability for positioning the loop over and around a target body organ and for manipulating the body organ. The strap means should atraumatically grip the body organ or tissue in a manner preventing the tightened loop from slipping on the organ or tissue as the device is used to manipulate the same. The strap also needs to be sealed inside the tube so that gases and fluids present inside the body cavity are prevented from escaping through the tube while the seal provides for strap movement along the tube. A locking means should be readily accessible to the user of the device and serve to lock the movement to maintain the loop size.

These and other aspects of the present invention will become increasingly apparent to those of ordinary skill in the art by reference to the following descriptions and to the drawings.

GENERAL DESCRIPTION OF THE INVENTION

The grasper device according to the present invention comprises a flexible strap that is initially housed inside a tube serving as a conduit means for the strap. The tube is moved through a cannula port so that a distal portion of the tube is inside the body cavity and a proximal, handle portion is outside the body. The strap is provided with a distal section having an attachment means provided at a terminal end thereof. Manipulative means operatively associated with the strap is manipulated adjacent to the proximal portion of the tube to deploy the distal strap section from the tube.

A second grasper device, preferably in the form of a laparoscopic forceps-type device, is introduced into the body cavity through a separate cannula port. This second grasper device is used to grasp and manipulate the terminal end of the distal strap section to mate the attachment means with a strap connection means provided either on the conduit means, the manipulative means or the strap itself to complete the loop, closed around the body organ The strap manipulative means is then manipulated to retract the strap into the tube and thereby tighten the loop to grasp the body organ. A locking means is provided on the tube to selectively maintain various sizes of the loop. There is also a sealing means in the tube that is provided to seal around either the strap or the manipulative means for the strap to prevent gases and fluids present inside the body cavity from moving through the tube to the proximal end thereof.

The strap section forming the loop is preferably provided with gripping formations such as ridges, studs, serrations, recesses or openings of various shapes and the like on the inner surface thereof or the strap can be provided with scalloped edges. Openings and recesses are preferred because they allow moisture trapped under the strap to escape while organ tissue pushes into the openings and recesses which function to atraumatically grip the organ tissue as the loop is tightened and then manipulated to move the body organ.

An important feature of the strap is that it is semi-rigid in a first plane aligned along the face of the strap, yet flexible in a second plane normal to the first. This rigidity allows the surgeon to easily maneuver the defined loop. A strap guide mounted on the tube restrains rotational movement of the strap, i.e., rotation of the strap around a longitudinal axis of the strap, and thereby allows the surgeon to manipulate the target organ in a controlled fashion.

The attachable and detachable strap provides the grasper device of the present invention as a particularly useful device in laparoscopic procedures for grasping and manipulating body organs that are not provided with an open end, but instead are attached to adjoining body tissue at both ends. Such organs include, but are not limited to, the colon and an umbilical cord within the uterus.

BRIEF DESCRIPTION OF THE DRAWINGS

FIG. 1 is a perspective view of one preferred embodiment of a grasper device 10 according to the present invention.

FIG. 2 is a broken, elevational view of the grasper device 10 shown in FIG. 1.

FIG. 3 is an enlarged, cross-sectional view of the distal portion of the grasper device 10 shown in FIG. 1 with the strap 16 detached from the strap connection means 34.

FIG. 3A is an enlarged, cross-sectional view of another embodiment of a strap connection means 34A according to the present invention.

FIG. 4 is an enlarged, cross-sectional view of the distal portion of the grasper device 10 shown in FIG. 3, but with the strap 16 attached to the connection means 34.

FIG. 5 is an enlarged, plan view of the distal portion of the grasper device 10 showing another embodiment of a strap attachment means detached from a connection means 112 according to the present invention.

FIG. 6 is an enlarged, cross-sectional view taken along line 6—6 of FIG. 5.

FIG. 7 is an enlarged, cross-sectional view of the distal portion of the grasper device 10 shown in FIG. 6, but with the strap attachment means attached to the connection means 112.

FIG. 8 is an enlarged, plan view of the distal portion of the grasper device 10 showing another embodiment of a strap attachment means detached from a connection means 152 according to the present invention.

FIG. 9 is an enlarged, cross-sectional view taken along line 9—9 of FIG. 8.

FIG. 10 is an enlarged, cross-sectional view of the distal portion of the grasper device 10 shown in FIG. 8, but with the strap attachment means attached to the connection means 152.

FIG. 11 is an enlarged, cross-sectional view of the distal portion of the grasper device 10 showing another embodiment of a strap attachment means detached from a connection means 164 according to the present invention.

FIG. 12 is an enlarged, cross-sectional view of the distal portion of the grasper device 10 shown in FIG. 11, but with the strap attachment means attached to the connection means 164.

FIG. 13 is an enlarged, cross-sectional view of the distal portion of the grasper device 10 showing another embodiment of a strap attachment means 192 detached from a connection means 180 according to the present invention.

FIG. 14 is an enlarged, cross-sectional view of the strap attachment means 192 attached to the connection means 180 shown in FIG. 13.

FIG. 15 is an enlarged, cross-sectional view taken along line 15—15 of FIG. 13.

FIG. 16 is an enlarged, cross-sectional view taken along line 16—16 of FIG. 13.

FIG. 17 is an enlarged, cross-sectional view of the distal portion of the grasper device 10 showing another embodiment of a strap attachment means 210 detached from a connection means 208 according to the present invention.

FIG. 18 is an enlarged, cross-sectional view of the distal portion of the grasper device 10 shown in FIG. 17, but with the strap attachment means 210 attached to the connection means 208.

FIG. 19 is an enlarged, cross-sectional view of the distal portion of the grasper device 10 showing another embodiment of a strap attachment means 232 detached from a connection means 220 according to the present invention.

FIG. 20 is an enlarged, cross-sectional view of the distal portion of the grasper device 10 shown in FIG. 19, but with the strap attachment means 232 attached to the connection means 220.

FIG. 21 is an enlarged, cross-sectional view of the distal portion of the grasper device 10 showing a strap attachment means 248 detached from a connection means 240 according to the present invention.

FIG. 22 is an enlarged, cross-sectional view of the distal portion of the grasper device 10 shown in FIG. 21, but with the strap attachment means 248 attached to the connection means 240.

FIG. 23 is an enlarged, partial plan view of the distal portion of the grasper device 10 showing a strap attachment means 252 detached from the connection means 240 according to the present invention.

FIG. 24 is an enlarged, partial plan view of the distal portion of the grasper device 10 shown in FIG. 23, but with the strap attachment means 252 attached to the connection means 240.

FIG. 25 is an enlarged, cross-sectional view taken along line 25—25 of FIG. 23.

FIG. 26 is an enlarged, cross-sectional view taken along line 26—26 of FIG. 24.

FIG. 27 is an enlarged, partial plan view of the distal portion of the grasper device 10 showing a strap attachment means detached from a connection means 260 according to the present invention.

FIG. 28 is an enlarged, partial plan view of the distal portion of the grasper device 10 shown in FIG. 27, but with the strap attachment means attached to the connection means 260.

FIG. 29 is an enlarged, cross-sectional view taken along line 29—29 of FIG. 27.

FIG. 30 is an enlarged, cross-sectional view taken along line 30—30 of FIG. 28.

FIG. 31 is an enlarged, partial plan view of the distal portion of the grasper device 10 showing a strap attachment means 286 detached from a connection means 280 according to the present invention.

FIG. 32 is an enlarged, partial plan view of the distal portion of the grasper device shown 10 in FIG. 31, but with the strap attachment means 286 attached to the connection means 280.

FIG. 33 is an enlarged, cross-sectional view taken along line 33—33 of FIG. 31.

FIG. 34 is an enlarged, cross-sectional view taken along line 34—34 of FIG. 32.

FIG. 35 is an enlarged, partial plan view of the distal portion of the grasper device 10 showing a strap attachment means 300 detached from a connection means 306 according to the present invention.

FIG. 36 is an enlarged, partial plan view of the distal portion of the grasper device 10 shown in FIG. 35, but with the strap attachment means 300 attached to the connection means 306.

FIG. 37 is an enlarged, cross-sectional view taken along line 37—37 of FIG. 35.

FIG. 38 is an enlarged, cross-sectional view taken along line 38—38 of FIG. 36.

FIG. 39 is an elevational view, partly in cross-section, of another embodiment of a grasper device 400 according to the present invention having a detachable support plate 412 and an associated strap means 420.

FIG. 39A is a partial perspective view of the distal end of the support plate 412 having a strap release means 416.

DETAILED DESCRIPTION OF THE INVENTION

Figure 40:
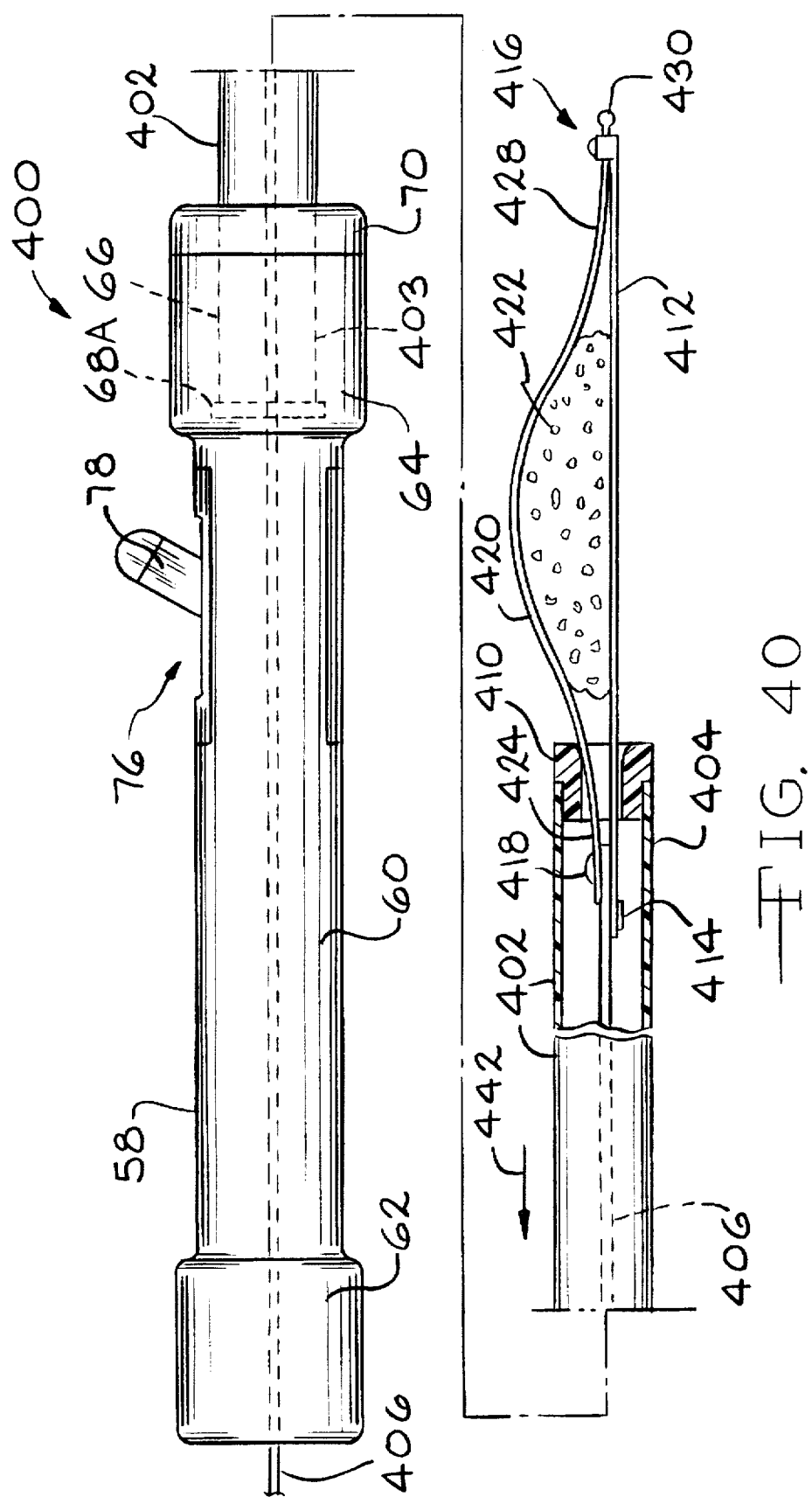
FIG. 40 is a perspective view, partly in cross-section, of the grasper device 400 of FIG. 39 showing the strap means 420 tightened about body organ 422.

As defined in this applications the word "distal" is used to describe that portion of the present grasper device which extends away from the user during operation thereof, and the word "proximal" is used to describe that portion of the grasper device that extends toward the user during the operation. Further, the terms "forward," "forwardly," "rearward," "rearwardly," "upper," "upwardly," "down," "downwardly," "lower," "right" and "left" simply refer to the orientation of FIGS. 1 to 39, and are not intended to be limiting.

Further throughout the various drawings, like members or parts are designated with like reference numerals.

Referring now to the drawings, FIGS. 1 to 4 show one preferred embodiment of a grasper device 10 according to the present invention. Grasper device 10 includes a conduit means comprising a tube 12 (FIGS. 2 to 4) disposed inside of a sleeve 14 preferably of an insulative, thermoplastic material. The tube 12 and sleeve 14 house a flexible strap 16 having a generally narrow width along its length between a first, proximal section 18 and a second, distal section 20. If desired, the second strap section 20 can be provided with memory characteristics that cause the second section 20 to assume a curved shape defining at least a partially closed loop upon deployment of the strap 16 from the tube 12, as described in U.S. patent application Ser. No. 08/402,344, filed Mar. 10, 1995, which is assigned to the assignee of the present invention and incorporated herein by reference As will be explained in detail hereinafter, the strap 16 is manipulated by means of a separate forceps-type grasper (not shown) to double the strap 16 back upon itself to define a loop 22. Although FIGS. 1 and 2 do not show the loop being completely closed, that is the intention of the present invention, as will be described herein. Loop 22 is useful in laparoscopic surgical procedures for grasping and manipulating a body organ and/or body tissue contained inside a body cavity, such as the abdomen, that are not provided with an open end, but instead are attached to adjoining body tissue at both ends. Examples of this type of body organ include the colon and an umbilical cord within the uterus. For a description of a laparoscopic grasper device that is particularly useful for grasping and manipulating body organs/body tissue that are open at one end, reference may be made to the previously mentioned U.S. Pat. No. 5,447, 684 to Jackson et al.

In use, the grasper device 10 is introduced into a body cavity, such as the abdomen, by means of a cannula port (not shown) that is inserted into the abdominal wall by means of a trocar (not shown), as is well known to those skilled in the art. For a more detailed description of such a trocar device and its use, reference may be made to U.S. Pat. No. 4,654,030 to Moll et al., the disclosure of which is hereby incorporated by reference. In that manner, tube 12, which is preferably made of metal or plastic, has a cylindrically shaped passage 24 (FIGS. 2 to 4) that extends along a longitudinal axis of tube 12 between a proximal open end (not shown) and a distal open end 26. Tube 12 is sized to tightly fit inside the insulative sleeve 14 which in turn fits inside the cannula port for introduction of the grasper device 10 into the body cavity with tube 12 serving as a conduit for the strap 16.

Strap 16 is made of a suitably flexible thermoplastic material which preferably is a polyacetal thermoplastic polymer. That way, the first strap portion 18 is useful as a manipulative means to move the strap 16 along and through the inside passage 24 to deploy the second strap section 20 out through the distal open end 26 of tube 12 and to retract the second section 20 inside tube 12, in a manner which will be described in detail hereinafter.

While not shown in FIGS. 1 to 4, a separate drive rod can be disposed inside passage 24 and be provided with a distal end attached to strap 16 for manipulation thereof. Such a drive rod is shown and described in other embodiments of the grasper device 400 and 450 shown in FIGS. 39, 39A, 40 and 41 which will be described in detail hereinafter.

As shown in FIGS. 1 and 2, strap 16 has a continuous inner surface with gripping formations in the form of perforations or openings 28 preferably having an elongated oval shape, provided at spaced locations or intervals along a grasping section of strap 16. Although openings 28 are shown extending completely through the thickness of strap 16, it should be understood that need not necessarily be the case. It is contemplated by the scope of the present invention that recessed formations (not shown) extending part way through the thickness of the strap 16 are also acceptable. In any event, the openings 28 serve as formations to facilitate gripping the colon or other body organ when loop 22 is positioned and tightened around the body organ, in a manner which will be described in detail presently. Although not shown in the drawings, it is also contemplated by the scope of the present invention that the gripping formations can comprise ridges, studs and serrations provided on the inner surface of strap 16 or that strap 16 can be provided with scalloped edges.

A guide means 30 for the strap means 16 is fitted into the distal open end 26 of tube 12 and serves to hold and direct the movement of strap 16 through tube 12 as the second strap section 20 is extended from and retracted into the tube 12 without allowing the strap 16 to rotate, i.e., guide 30 prevents strap 16 from rotating about its longitudinal axis and about the longitudinal axis of the tube 12. This provides the surgeon or attending person with control of the strap 16 and formed loop 22 so that during a surgical procedure, the loop 22 is maneuverable with a body organ, to thereby cradle and manipulate the organ.

As shown in FIG. 4, one of the openings 32, preferably the one proximate the terminus of the second section 20 of strap 16 serves as an attachment means. This attachment aperture 32 provides for attaching the second section 20 of the strap 16 to a strap connection means 34 provided on the guide means 30 to complete the loop 22, as will be explained in detail presently.

In particular, the guide means 30, as shown in cross-section in FIGS. 2 to 4, is formed as a unitary body that is preferably made of a metal or a thermoplastic material, and, if thermoplastic, preferably it is an acetal material. Guide 30 has a cylindrically shaped insert portion 36 having an elongated and narrow opening 38 and a tip portion 40 having outwardly diverging passages 42 and 44 that extend from opening 38 to an outer face 46 to form a Y-shape cross-sectional opening network. The passages 42 and 44 each have curved or rounded corners and are dimensioned to allow for sliding and guiding movement of the strap 16 therealong while preventing the strap from rotating about its longitudinal axis.

Insert portion 36 has an outer diameter substantially equal to the inner diameter of tube 12 so as to be in a snug-fitting relationship with the inside passage 24 thereof and includes a first annular ledge 48 abutting the distal open end 26 of tube 12 and a second annular ledge 50 abutting the distal open end of sleeve 14. To insure that the guide 30 does not inadvertently separate from its snug-fitting relationship with the inside passage 24, the tube 12 is preferably swaged down into the insert portion 36. Further, the guide 30 can be provided as a selectively removably mounted member in the distal open end of the tube 12, as described in detail in the previously referenced application Ser. No. 08/402,344.

A channel 52 is provided into the upper surface of the guide 30 to a depth sufficient to capture a strap hook 54 comprising the connection means 34. The strap hook 54 has a foot 56 laying along the inner face of guide 30 with the opposite, hook end disposed generally parallel to the upper angled surface of passage 42. That way, when the attachment aperture 32 receives the hook 54, the strap 16 is captured between the upper angled surface of passage 42 and the hook end (FIG. 4). FIG. 3A shows another embodiment of a strap connection means 34A according to the present invention comprising a hook 54A embedded or otherwise secured to the guide 30 and disposed generally parallel to the upper angled surface of the passage 42.

In the grasper device 10 illustrated in FIGS. 1 to 4, the strap connection means 34 preferably is provided on the guide means 30. Various additional embodiments of the connection means provided on the guide means are shown in FIGS. 5 to 16. In a broader sense, however, and in accordance with the scope of the present invention, the strap connection means can be provided at other locations such as on the distal end of the conduit means 12, on a manipulative means comprising a drive rod for the strap 16 disposed in a movable relationship inside the tube 12 and, even on the strap itself. These latter two aspects of the present invention will be described with respect to FIGS. 39 and 39A to 41,and 17 to 38, respectively.

As shown in FIGS. 1 and 2, a handle 58, preferably made of a metal or plastic material is mounted on the proximal portion of tube 12. Handle 58 has a cylindrically shaped intermediate portion 60 disposed between proximal and distal enlarged portions 62 and 64, respectively. An inner opening 66 (shown in dashed lines in FIG. 2) extends longitudinally along the distal enlarged portion 64 and is sized to receive the proximal portions of the tube 12 and the associated sleeve 14 in a snug-fitting relationship. The proximal open end of the tube 12 and the sleeve 14 capture a sealing means 68 in the form of a disc-like member (shown in dashed lines in FIG. 1) having a slit that fits snugly around the perimeter of strap 16. Sealing means 68 serves to seal around the strap 16 to prevent gases and fluids present inside the body cavity from moving through the tube 12 to the proximal open end thereof when the distal portion of the tube 12 is inserted into the body cavity. The sealing means 68 also allowing movement of the strap means 14 along the tube 12.

A retainer 70 is threaded onto the end of the distal portion 64 of handle 58 surrounding the sleeve 14 and tube 12 to lock them to the handle 58 mounted in the inner opening 66. Retainer 70 is also preferably made of a metal or plastic material, and if plastic, preferably it is a polyacetal material. A channel (not shown) extends longitudinally along the remaining length of handle 58 to the end of the proximal portion 64 thereof.

A threaded opening (not shown) is provided in the end of the proximal portion 62 of handle 58 and receives a threaded member 72 extending through a terminal aperture provided in the first strap section 18 to secure the strap 16 to the handle 58. This construction provides a manipulatable loop 74 that is intended to be grasped to move the strap 16 along the handle channel and the opening 24 through the tube 12 to thereby deploy and retract the strap 16 from the guide 30.

There is also provided a locking means 76 that is accessible from a remote location outside the body cavity to selectively allow and prevent movement of the strap 16 along and through the inner passage 24 of the tube 12 to deploy and retract the second strap section 20 from the channel opening 44 in the guide 30. The locking means 76 is movable to an enabled or engaged position (FIGS. 1 and 2) to prevent movement of strap 16 along the inner passage 24 of tube 12 and to a disabled or disengaged position (not shown) to allow such movement of strap 16. More specifically, in this embodiment of the grasper device 10 of the present invention, the locking means comprises a cam lock of the type shown in FIG. 33 of the previously referenced U.S. Pat. No. 5,447,684 to Jackson et al. Other locking means are also contemplated by the scope of the present invention, as described in the Jackson et al. patent and the previously referenced application Ser. No. 08/402,344.

To enable the locking means 76, the arm 78 is moved in a forwardly direction, towards the distal open end 26 of the tube 12. This causes the cam surface (not shown) of the cam to contact the strap 16 and secure the strap 16 against an inner surface of the tube 12. When it is no longer desired to lock the strap 16 in position, the arm 78 is moved in an opposite, rearwardly direction to release the cam surface from contact with the strap 16 against the tube 12.

When cam lock is in the disengaged position (not shown), released from contact with strap 16 and with the distal portion of tube 12 adjacent to a target body organ, the manipulatable loop 74 formed by the first section 18 of strap 16 is manipulatable in a forwardly direction, as indicated by the arrow 80 in FIG. 2. to extend the second strap section 20 out through the passage 44 in the guide face 30. The strap attachment aperture 32 is then positionable on the strap hook 54 comprising the connection means 34 by appropriate manipulation using a laparoscopic forceps-type device (not shown), which has been separately introduced into the body cavity device, to complete loop 22.

In the case of the second strap section 20 having memory-curved characteristics, such forward movement of the first strap section forms loop 22 in a partially extended relationship around the body organ due to the memory-curved characteristics. Handle 58 is then manipulatable to move the partially formed loop 22 to a desired position axially along the length of the body organ and the strap attachment aperture 32 is attachable to the strap connection means 34 to complete the loop 22.

With the loop 22 secured to the strap hook 54, the first strap section 18 is movable by hand in a rearwardly direction, as indicated by arrow 82 in FIG. 2, to tighten the loop 22 around the body organ and permit strap openings 28 to grasp and lock onto the body organ. The surgeon is then able to perform the intended surgical procedure by manipulating grasper 10 to move the organ as needed.

In use, the grasper device 10 of the present invention provides for holding and manipulating a body organ inside a body cavity from a remote location outside the cavity during a surgical procedure. In that respect, grasper device 10 is first inserted into the body cavity through a cannula port (not shown) so that the distal portion of the tube 12 is inside the body cavity while the proximal tube portion and handle 58 are outside the body cavity at the remote location. To facilitate movement of the grasper device 10 through the cannula port, strap 16 is preferably housed inside tube 12 with the terminus of the second strap section 20 disposed proximate the outer guide face 46 of passage 44.

Typically, in a laparoscopic surgical procedure, carbon dioxide is pumped into the abdomen to separate the body organs contained therein from the abdominal sidewall. Thus, sealing means 68 serves to contain this carbon dioxide gas and other body fluids to prevent them from moving through the inner passage 24 in tube 12 to the proximal open end thereof.

With the distal tube portion inside the body cavity and the locking means 76 disengaged, the manipulatable loop 74 comprising the first section 18 of strap 16, which extends from the proximal open end of handle 58, is manipulated from the remote location to move strap 16 in a forwardly direction, as indicated by arrow 80 in FIG. 2, to push the strap 16 out through the guide passage 44 to extend the second strap section 20 out through the outer guide face 46. Passage 44 in guide 30 serves to direct this sliding movement without allowing strap 16 to rotate about its longitudinal axis. In other words, there is no rotation of strap 16 relative to the longitudinal axis of tube 12 which provides the surgeon with control of the second strap section 20. In the case of the second strap section 20 have memory-curved characteristics, by manipulating handle 58 and the first section 18 of strap 16, the surgeon is able to deploy the second strap section 20 to begin forming loop and position the partially defined loop around a target body organ. Since strap 16 is relatively rigid in a plane normal to its width, loop 22 can then be moved axially along the body organ to a desired position.

Whether or not the second strap section 18 is provided with memory-curved characteristics, in order to complete the loop 22 around the body organ, it is necessary for the surgeon or other attending person to grasp ahold of the terminal end of strap 16 adjacent to attachment aperture 32 by means of a second manipulation means preferably comprising a pair of laparoscopic forceps (not shown). These forceps are manipulated to move the terminal end of strap 16 into passage 42 a distance such that the attachment aperture 32 is in registry with the hook end. The strap 16 is then pulled in an upwardly and forwardly direction to fit over the aperature 32 and around the hooked end of hook 54 until that portion of the strap 16 distal of the attachment aperture 32 is cradled or captured between the guide surface of passage 42 and the hooked end.

The first section 18 of strap 16 is then pulled in a rearwardly direction, as indicated by arrow 82 in FIG. 1, to tighten loop around the body organ for holding the body organ. As this happens, moisture trapped under strap 16 escapes into the formations, such as openings 28 and organ tissue pushes up into the openings 28, which in conjunction with the continuous inner surface of the strap 16 serve to atraumatically grip the body organ.

With the body organ held in the loop 22, the surgeon can actuate the locking means 76 to the enabled position (FIGS. 1 and 2) to thereby lock the loop 22 in position around the body organ. The surgeon is then able to manipulate the handle 58 to move the body organ as needed during the surgical procedure.

At such time as grasper device 10 is no longer needed to manipulate the body organ, the locking means 76 is moved to a position released from contact with the strap 16 so that the first section 18 of strap 16 can be first pushed in a forwardly direction, as indicated by arrow 80 of FIG. 2, to open loop 22. The forceps device is manipulated to remove the strap from engagement with the hook by moving the attachment aperture 32 off of the hooked end, and the handle 58 is manipulated to remove the strap 16 from around the body organ. Then, the strap 16 is pulled rearwardly, in the direction of arrow 82 in FIG. 2, to retract the strap 16 into guide 30. The grasping device 10 is next pulled out of the body cavity through the cannula port, and the surgical procedure is completed as required.

At such time as the use of the grasper device 10 is no longer needed in the surgical procedure, the grasper device 10 is preferably disposed of. However, it will be apparent to those skilled in the art that reusable designs for the grasper device are contemplated within the scope and breadth of the present invention.

FIGS. 5 to 7 show another embodiment of the distal portion of the grasper device 10 of the present invention including a guide means 100 fitted into the distal open end 26 of tube 12 and secured in place by a pin 102 (shown in dashed lines in FIG. 5). Pin 102 is fitted into a cross-bore 104 provided in the insert portion 106 of guide 100 and disposed normal to the longitudinal axis of tube 12. The opposed ends of pin 102 extend beyond the side wall of the insert portion 106 and are received in opposed openings 108 (shown in dashed lines in FIG. 5) provided in the distal portion of tube 12 to thereby secure the guide 100 in the distal open end 26 thereof. The guide 100 serves to direct movement of the strap 16 through the tubes 12 without allowing the strap to rotate about its longitudinal axis in a similar manner as guide 30 in FIGS. 1 to 4.

Guide 100 further comprises a tip portion 110 having a strap connection means 112 including a plate 114 supporting a pair of side-by-side posts 116 and 118, each having a cantilever 120 and 122, respectively, extending rearwardly and facing a forwardly extending cantilever 124. Forward cantilever 124 extends laterally across the width of the tip portion 110 to provide a lateral recess 126 disposed between itself and the side-by-side posts 116, 118 which are themselves spaced apart to provide a longitudinal recess 128 therebetween. The lateral recess 126 communicates with the longitudinal recess 128.

The strap 16 further includes a web 130 connecting to opposed wings 132 forming an arrow head at the terminus of the second strap section 20 providing a strap attachment means that is received or otherwise mated with the strap connection means 112 to form a loop (not shown in FIGS. 5 to 7). A downwardly angled surface 134 at the forward end of the strap channel 136 through the tip portion 110 of guide 100 helps the deployed strap 16 to curve or arch into a well defined loop.

In use, the strap attachment means is mated to the connection means 112 by appropriate manipulation of the strap 16 with the laparoscopic forceps (not shown) with the web 130 received in the longitudinal recess 128 and the arrow head received in the lateral recess 126 such that the wings 132 are align with the posts 116, 118. Then, movement of the second strap section 20 in a forwardly direction, as indicated by arrow 134 in FIG. 7, captures the arrow head in the lateral and longitudinal recesses 126 and 128, respectively, with the wings 132 nested between the plate 114 and the cantilevers 120, 122 such that the posts 116 and 118 block the wings 132 from releasing therefrom to secure the strap attachment means to the connection means 110 to complete the loop. As is apparent to those skilled in the art, reversing this movement causes the strap 16 to release from the connection means 112 to open the loop.

FIGS. 8 to 10 show another embodiment of the distal portion of the grasper device 10 of the present invention including a strap guide means 140 snuggly fitted into the distal open end 26 of the tube 12. A pair of side-by-side fins 142 and 144 extend upwardly from the tip portion 146 of the guide 140 to project towards a curved face 148 joining to a horizontally disposed recess 150 between the fins 142, 144 thereby comprising a strap connection means 152. A protuberance 154 is provided at the end of each fin 142, 144. The strap 16 has the web 156 connecting to opposed wings 158 forming an arrow head at the terminus of the second strap section 20 providing a strap attachment means that is mated with the strap connection means 152 to form a loop (not shown).

To form a loop, the attachment means is mated with the connection means 152 by appropriate manipulation of the strap 16 with the laparoscopic forceps (not shown) such that the web 156 is received in the longitudinal recess 160 between the fins 142, 144 and the arrow head is received between the curved face 148 and the protuberances 154. The protuberances 154 help to retain the wings in this position blocked against the fins 142, 144. Reversing the above described movement causes the strap 16 to release from the connection means 152 to open the loop, as is apparent to those skilled in the art.

FIGS. 11 and 12 show another embodiment of the distal portion of the grasper device 10 of the present invention that is similar to the structure shown in FIGS. 8 to 10. However, in this embodiment, the upper section of the tip portion 162 of the strap guide 160 has a strap connection means 164 including a generally elongate V-shaped recess 166 disposed between a pair of side-by-side fins (only one fin 168 is shown in FIGS. 11 and 12) each having rearwardly projecting cantilevers 170. The tip portion 162 of the guide 160 has a pair of protuberances 172 opposite the cantilevers 170. The protuberances 172 help retain the wings 174 of the arrow head 176 blocked against the fins 168 to mate the attachment means with the connection means 164 (FIG. 12) to provide a loop (not shown).

FIGS. 13 to 16 show another embodiment of the distal portion of the grasper device 10 of the present invention including a strap connection means 180 comprising a plate 182 which is sized to slide into a pair of slots 183 (shown in dashed lines in FIG. 15) provided in the side wall of tube 12 and extending parallel to the longitudinal axis of the tube 12. A tongue 184 depends from the proximal end of plate 182 while the distal end of plate 182 supports an inclined extension 186 that forms into a crook 188 having an arrow head 190 at the end thereof.

To form a loop, a attachment aperture 192 provided at the terminus of the second strap section 20 is moved into registry with and over the arrow head 190 by appropriate manipulation thereof with the laparoscopic forceps (not shown). In this position, the strap 16 surrounds the crook 188 while the arrow head 190 prevents the inadvertent release of the attachment aperture 192 from the connection means 180. However, while the arrow head 190 is sized to prevent the inadvertent release of the attachment aperture 192 therefrom, it does enable the second strap section 20 to release from the arrow head 190 under a positive force such as is provided by appropriate manipulation of the strap 16 with the laparoscopic forceps device to release the attachment aperture 192 from the connection means 180 to open the loop.

FIG. 17 to 38 show various embodiments of the grasper device 10 of the present invention wherein the strap connection means is provided on the strap 16 itself. In FIGS. 17 and 18, a guide means 200 is snuggly fitted into the distal open end 26 of the tube 12. The guide 200 has a opening 202 extending therethrough and along the longitudinal axis of the guide 202 and tube 12 forming into a fan-shaped opening 204 leading to an end face 206 thereof. The guide opening 204 is sized to direct sliding movement of the strap 16 without allowing the strap 16 to rotate about its longitudinal axis.

The strap 16 is further provided with a series of spaced openings or slots 208 extending completely through the thickness of the strap 16. These openings 208 serve as a strap connection means that receive an attachment means 210 connected to the distal end or terminus of the strap 16. The attachment means 210 comprises a clip 212, preferably of a metal material, to provide the clip 212 with spring-like properties. Clip 212 is crimped onto the end of strap 12 and has an arm 214 that bears against the strap 12 spaced from the terminus thereof. The openings 208 are spaced along the strap 16 at intervals such that to form a loop (not shown), the end of arm 214 is moved through a first opening 208 and curved around and through a next adjacent opening 208 to capture the strap 12 between the clip 212 and the strap terminus, as shown in FIG. 18.

Typically, the strap 16 is initially deployed with the clip 212 connected to the strap openings 208 and the guide opening 204 providing for movement of the clip 212 connected to the strap 16 therethrough. The clip 212 is then disconnected from the strap openings 208, moved around the body organ and reconnected to grasp the organ. A similar sequence of steps is applicable for the disconnection and reconnection of the respective strap attachment means and the connection means shown in FIGS. 19 to 38 moved out through the guide opening 204 in guide 200.

FIGS. 19 and 20 show another embodiment of a strap connection means 220, similar to that shown in FIGS. 17 and 18, except that the clip 222 has a fastener portion 224 received in an opening 226 disposed adjacent to the terminus of the strap 16 and anchored in a detent 228. The fastener portion 224 of clip 222 is crimped in this position to further secure the clip 222 on the strap 16. In use, the arm 230 of clip 222 is moved though an attachment aperture 232 provided in the strap 16 by appropriate manipulation of the strap 16 with the laparoscopic forceps (not shown) such that the arm 230 bears against the strap 16 on the side of the fastener portion 224 opposite the clip 222 (FIG. 20). In this position, the strap 16 is captured between the arm 230 and the clip fastener portion 224 to close the loop and prevent inadvertent opening thereof. To open the loop (not shown), the strap 16 is manipulated to move the aperture 232 along the arm 230 and past the end thereof.

FIGS. 21 and 22 show another embodiment of a strap connection means 240 provided on the strap 16 and comprising a clip 242 passed through a pair of openings 244 in the strap 16 and crimped thereto. The arm 246 of clip 242 bears against the strap 16 towards the guide 200. The strap 16 is provided with a series of spaced openings 248 serving as attachment apertures that are mated with the clip 242 by appropriate manipulation of the strap 16 with the laparoscopic forceps (not shown) such that the end of arm 246 bears against that portion of the strap 16 immediately proximate the connection of clip 242 to the strap 16, as shown in FIG. 22.

As is apparent to those skilled in the art, when the arm 246 of clip 242 is received in one of openings 248 in strap 16 spaced from the opening 248 immediately proximate the strap terminus, the end of arm 246 bears against the strap 16 adjacent to the opening receiving the arm 246. However, the biasing force of the clip arm 246 bears firmly against the strap 16 to prevent release of the strap 16 from the connection means 240 to prevent the loop (now shown) from inadvertently opening. At such time as it is desired to open the loop, the previously described forceps device is manipulated to grasp the strap 16 adjacent to the attachment aperture 248 and to move the aperture 248 along the arm 246 with enough force to overcome the bias of the clip 242 to release the strap 16 therefrom.

FIGS. 23 to 26 show another embodiment of the present invention having the strap connection means 240, similar to that shown in FIGS. 21 and 22. However, in this embodiment of the present invention the attachment means 252 is provided by an eyeclasp 254 secured on the terminus of the second strap section 20. To provide a loop (not shown), the eye 256 of clasp 254 is moved over and past the end of the arm 246 of the clip 242 by appropriate manipulation of the strap 16 with the laparoscopic forceps (not shown) to capture the clasp 254 between the arm 246 and the strap 16. To open the loop, the eye-clasp 254 is moved in a reverse direction along and past the end of the arm 246 of the clip 242, as is apparent to those skilled in the art.

FIGS. 27 to 30 show another embodiment of a strap connection means 260 provided on the strap 16 and comprising a keyholeshaped aperture 262 having a rounded portion 264 facing the guide 200 and communicating with an elongate oval portion 266. The strap attachment means comprises a web 268 connecting to opposed wings 270 forming an arrow head provided at the terminus of the second strap section 20. In use, the arrow head is received in the rounded opening 264 and the web 268 is moved along the oval portion 266 of the keyhole aperture 262 until the arrow head contacts the end of the oval 266, spaced from the rounded opening 264 by appropriate manipulation of the strap attachment means by the laparoscopic forceps (not shown). The opposed wings 270 are wider than the width of the oval 266 which blocks the wings 270 and prevents the strap attachment means from releasing from the connection aperture 262 upon formation of the loop (not shown).

FIGS. 31 to 34 show another embodiment of a strap connection means 280 comprising a rivet 282 secured through the thickness of the strap 16 and having an enlarged head 284 spaced above the continuous surface thereof. The terminal end of the second strap section 20 has an attachment means 286 including a keyhole-shaped aperture 288 comprising an elongate oval portion 290 proximate the terminus of the strap 16 and communicating with a rounded opening 292.

In use, the attachment means 286 is mated with the connection means 280 to form a loop (not shown) by appropriate manipulation of the second strap section 20 with the laparoscopic forceps (not shown) by first moving the rounded opening 292 into registry with the enlarged head 284 of rivet 282. The continuous surface of the strap 16 at the terminal end thereof is next brought into contact with the continuous surface of the strap 16 at the rivet 282. Then, the elongate oval portion 290 is moved along the rivet 282 until the end of the oval 290 abuts the rivet 282. The enlarged head 284 is wider than the width of the oval 290 to thereby secure the attachment means 286 to the connection means 280 to form the loop. Reversing the above described movement causes the strap 16 to release from the connection means 280 to open the loop, as is apparent to those skilled in the art.

FIGS. 35 to 38 show another embodiment of an attachment means 300 comprising a rivet 302 secured to the terminal end of the second strap section 20 and having an enlarged head 304 spaced from the continuous surface thereof. The strap 16 is further provided with a connection means 306 comprising a series of keyhole shaped apertures 308 (only one aperture 308 is shown in FIGS. 35 to 38) disposed through the strap 16 thickness and spaced from the terminal end thereof. The keyhole apertures 308 each include an elongate oval portion 310 communicating with a rounded opening 312 wherein the rounded opening 312 faces the guide 200.

In use, the connection means 306 is mated with the attachment means 310 by appropriate manipulation of the strap attachment means 300 by the laparoscopic forceps (not shown) by first moving the enlarged head 314 of the rivet 302 through the rounded opening 312 until the continuous surface of the strap 16 contacts itself. The strap 16 is then manipulated to move the enlarged head 304 along the oval portion 310 to the end thereof. As in the embodiment shown in FIG. 31 to 34, the enlarged head 304 is wider than the width of the oval 310 to thereby secure the connection means 306 to the attachment means 300 to form a loop (not shown). Reversing the above described movement causes the strap 16 to release from the connection means 306 to open the loop, as is apparent to those skilled in the art.

FIGS. 39 and 39A and 40 show another embodiment of a grasper device 400 of the present invention. This grasper device 400 comprises a tube 402 having a proximal portion 403 (shown in dashed lines in FIG. 40) and a distal portion 404 providing an inner opening or lumen extending between respective proximal and distal open ends and along the longitudinal axis thereof. The proximal tube portion is connected to a handle 58 previously described with respect to in a similar manner as the grasper device 10 shown in FIGS. 1 and 2, having a cylindrically shaped intermediate portion 60 disposed between the proximal and distal enlarged portions 62 and 64, respectively. An inner opening 66 (shown in dashed lines in FIG. 40) extends longitudinally along the distal enlarged portion 64 and is sized to receive the proximal portion 403 of tube 402 in a snug-fitting relationship. A manipulative means comprising a drive rod 406 is disposed inside the tube 402 and handle in a movable relationship therewith. The drive rod 406 is, for the majority of its length, a cylindrically shaped member having a circular cross-section dimensioned and disposed to be received in the inner opening of tube 402 and extending to a rectangular shaped distal portion 408.

The proximal open end of the tube 402 captures a sealing means 68A in the form of a disc-like member (shown in dashed lines in FIG. 40) having an opening that fits snugly around the perimeter of the drive rod 406. Sealing means 68A serves to seal around the drive rod 406 to prevent gases and fluids present inside the body cavity from moving through the tube 402 to the proximal open end thereof when the distal portion of the tube 402 is inserted into the body cavity. The sealing means 68A also allows movement of the drive rod 406 along the tube 402. The retainer 70 is threaded onto the end of the distal portion 64 of handle 58 surrounding the tube 402 to lock the tube to the handle 58 mounted in the inner opening 66.

There is also provided the locking means 76 on the handle 58 which is selectively movable between enabled and disabled positions to respectively prevent and allow movement of the drive rod 406 along and through the tube 402 in a similar manner as previously described with respect to the strap 16, as shown in FIGS. 1 and 2.

A guide means 410 is provided at the distal open end of tube 402. Guide 410 is similar to the guide 30 (FIG. 1 to 4), guide 100 (FIGS. 5 to 7), guide 140 (FIGS. 8 to 10), guide 160 (FIGS. 11 and 12) and guide 200 (FIGS. 17 to 38) in that it serves to hold and direct sliding movement of the drive rod 406 through tube 402 while preventing the drive rod 406 from rotating about its longitudinal axis, i.e., the length of the drive rod 406 relative to the longitudinal of tube 402 as the drive rod 406 is moved in both forwardly and rearwardly directions along and through the handle and the tube 402. The guide 410 is preferably removably mounted in the distal open end of tube 402, as described in detail in the previously referenced application Ser. No. 08/402,344. It is also contemplated by the scope of the present invention that the guide 410 can be press-fitted or swaged into the distal open end of the tube 402 in a similar manner as guide 30 is fitted into the distal open end 26 of tube 12 (FIGS. 1 to 4).

A detachable support plate 412 comprising the manipulative means is attached to the distal portion 408 of the drive rod 406 on the under side thereof. There, the drive rod 406 is provided with a rivet 414 having a head that depends beyond the surface thereof to be received in a keyhole opening (not shown) in the proximal portion of the plate 412. The opposite, distal end of the plate supports a strap release means 416. The drive rod 406 is further provided with a second rivet 418 having a head extending beyond the upper surface of the support plate 412.

A flexible strap 420, similar to strap 16 (FIGS. 1 to 38), is removably associated with the drive rod 406 and the support plate 412 to hold a body organ 422 against the plate 412. In that respect, the first section 424 of strap 420 is provided with a series of eyelet openings 426 that are sized to mate with and thereby receive the rivet 418. Thus, the eyelet openings 426 provide a strap attachment means that removably mates with the connecting rivet 418 to attach the strap 420 to the drive rod 406. The second section 428 of the strap 420 is provided with an enlarged head 430 that is larger in size than the opening in the strap release means 416 provided at the distal end of the support place 412. As shown in FIG. 39A, the strap release means 416 comprises a movable tang 432 extending from the support plate 412 and having a rivet 434. The rivet 434 coacts with a keyhole opening 436 disposed in an arm 438 to releasedly attach the arm 438 to the finger 432 with the second section 428 of the strap 420 captured between the arm 438 and the plate 412 wherein the enlarged head 430 prevents the inadvertant release of the strap 420 from the support plate 412.

Figure 41:
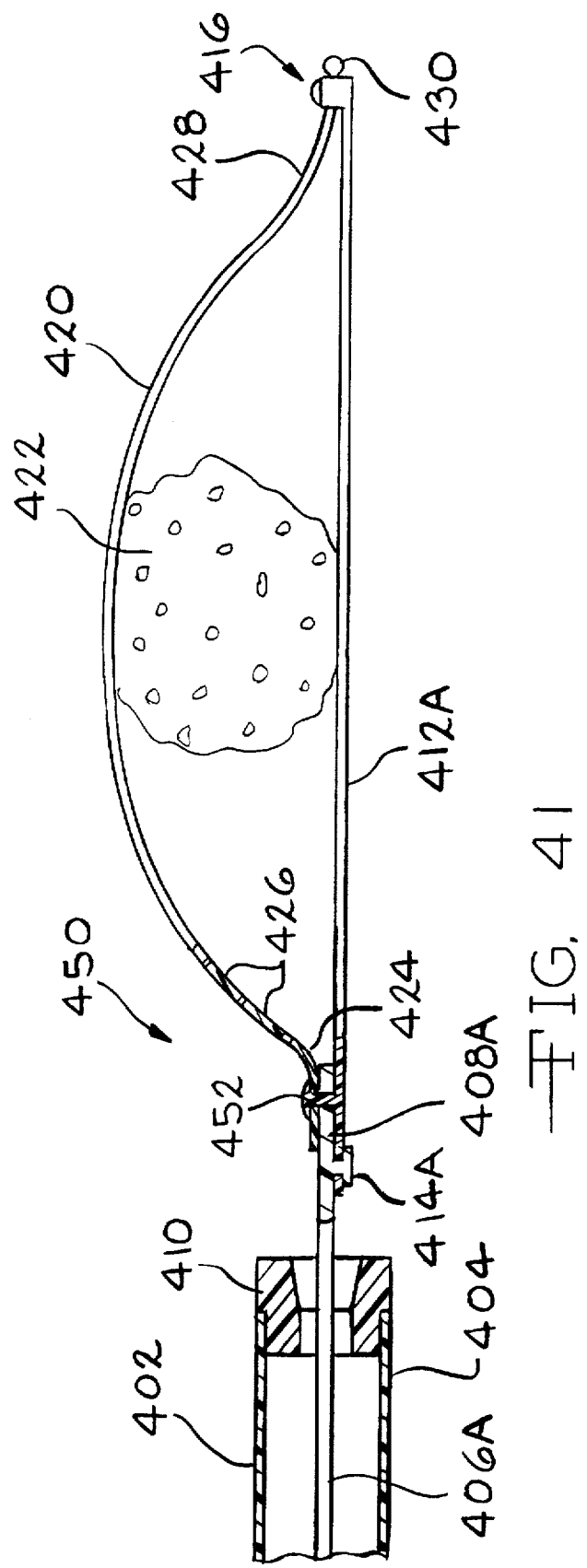
FIG. 41 is a perspective view, partly in cross-section, of another embodiment of the grasper device 450 according to the present invention.

Although not shown in FIGS. 39,40 and 41 strap 420 has a continuous inner surface provided with gripping formations in the form of perforations or openings similar to openings 28 in strap 16. The gripping formations in strap 420 need not extend completely through the strap thickness, and they serve as formations to facilitate gripping the body organ 422 at such time as the strap 420 is positioned to hold the body organ 422 against the support plate 412. This is useful when the body organ 422 is being subjected to a stapling operation to attach sections of the body organ together, for example.

Thus, the distal portion 404 of the grasper device 400 is initially inserted into the body cavity with both the first and second strap sections 424 and 428 connected to the respective distal portion 408 of the drive rod 406 and the strap release means 416 at the distal end of the support plate 412. The support plate 412 is attached to the drive rod 406 by the rivet 414 and mating keyhole structure. With the drive rod 406 withdrawn into the tube 402 such that the distal end of the support plate 412 is disposed at the distal open end of the tube 402, the drive rod 406 is moved in a forwardly direction, as indicated by arrow 440 in FIG. 39, out through the tube 402 to thereby cause the rivet 418 and the first strap section 424 to move out through the distal open end of the tube 402.

Once deployed, a separate grasper device (not shown) such as a forceps-type device previously introduced into the body cavity through a separate cannula port, is manipulated to grasp ahold of the first strap section 424 to move the keyhole eyelet opening 426 off of the rivet 418 and thereby open the strap 420. The grasper device 400 is further manipulated to maneuver the support plate 412 under the body organ 422 and the free, first section 424 of the strap 420 is then moved over the body organ and again mated to the drive rod 406 with the rivet 418 received in one of the eyelet openings 426 to secure the strap 420 holding the body organ against the support plate 412.

As shown in FIG. 40, with strap 420 in place, the drive rod 406 is moved in a rearwardly direction, as indicated by arrow 442 in FIG. 40, to move drive rod 406 along within tube 402 and the handle to tighten the strap 420 against the guide 410 and thereby grasp and hold the body organ. As this happens, moisture trapped under strap 420 escapes into the gripping formations (not shown), as previously described, and the organ tissue pushes up into the formations, which in conjunction with the continuous inner strap surface serve to atraumatically grip the body tissue.

During the foregoing, drive rod 406 is prevented from rotating about its longitudinal axis by guide 410 as previously described. The surgeon is then able to actuate the locking means 76 to lock the drive rod 406 in position with the strap 420 and support plate 412 holding the body organ 422. The surgeon is then able to perform the intended surgical procedure by manipulating the organ as needed.

When grasper device 400 is no longer needed to manipulate the body organ, the locking means 76 is disabled so that the drive rod 406 is once again movable in a forwardly direction, as indicated by arrow 440 in FIG. 39, to remove some of the tension off of strap 420. The previously mentioned forceps grasper device (not shown) is again manipulated to disconnect the first section 424 of strap 420 from the distal portion of the drive rod 406 by removing the one mated eyelet opening 426 from the rivet 418 to release the strap 420 from the body organ. The first strap section 424 is then reconnected to the drive rod 406 free of the body organ 422. The drive rod 406 is now moved in a rearward direction, as indicated by arrow 440, 442 in FIG. 40 to a fully retracted position inside tube 402 to retract the strap 420 and the support plate 412 into guide 410 and tube 402 before grasper device 400 is removed from the body cavity by moving it out through its cannula port (not shown). Of course, the forceps device can be used to manipulate the movable finger 432 to release the rivet 434 from the keyhole opening 436 in arm to release the second strap section 428 from the support plate 412 and to reconnect the same to hold the body organ 422 as needed.

FIG. 41 shows another embodiment of a grasper device 450 of the present invention. Grasper device 450 is similar to the grasper device shown in FIGS. 39, 39A and 40 except that the series of eyelet openings 426 provided in the straps 420 are mated with and received by a rivet 452 provided on a support plate 412A detachably supported to the distal portion 408A of a drive rod 406A by a rivet 414A received in a keyhole opening (not shown) in the proximal portion of plate 412A.

During a surgical procedure, the separate grasper device (not shown) previously introduced into the body cavity through a separate cannula port is manipulated to grasp ahold of the first strap section 424 to move the eyelet opening 426 off of the rivet 452 to thereby open the strap 420. The grasper device 450 is manipulated to maneuver the support plate 412A under the body organ and the free, first section 424 of the strap 420 is then moved over the body organ and again mated to the support plate 412A with the rivet 452 received in one of the eyelet openings 426 to secure the strap holding the body organ against the support plate 412A.

As is the case with the previously described grasper device 10, the grasper devices 400 and 450 are preferably disposed of after a surgical procedure. However, it is contemplated by the scope of the present invention that those skilled in the art will understand that parts of the grasper devices 400 and 450 can also be reusable.

It is appreciated that various modifications to the inventive concepts may be apparent to those skilled in the art without departing from the spirit and scope of the present invention.

What is claimed is:

1. A medical device that is insertable into a body cavity to grasp and manipulate a body organ located therein from a remote location outside the cavity during a surgical procedure, which comprises:

a) elongated conduit having a surrounding sidewall providing an inside passage extending to proximal and distal portions having respective spaced apart open ends, wherein the proximal portion of the conduit provides a handle for inserting the distal portion into the body cavity and for manipulating the distal portion from the remote location;

b) flexible strap having a width and a thickness so as to be received in a movable relationship in the inside passage of the conduit, wherein the strap has a first section and a second section; and c) manipulator operatively associated with the strap and manipulatable from the remote location to move the strap along the inside passage of the conduit between a fully retracted position with the strap substantially housed inside the conduit and a deployed position with the strap completely outside the conduit, wherein the first section of the strap has a first attachment that is attachable to and detachable from a first strap connection provided on the manipulator at an intermediate position located between the proximal and distal portions thereof with the strap in the deployed position and wherein a second attachment provided on the strap is attachable to and detachable from a second strap connection provided at a distal end of the manipulator to thereby define an enclosure adjacent to the distal open end of the conduit that is manipulatable in a surrounding relationship with respect to the body organ to manipulate the same.

2. The medical device of claim 1 wherein the manipulator comprises a drive rod and a support plate with the drive rod having a proximal portion positioned adjacent to the proximal portion of the conduit and a distal portion detachably connected to the supoort plate, and wherein the first section of the strap is attachable to and detachable from the first strap connection provided on the drive rod at the intermediate position located between the proximal and distal portions of the manipulator and with the second section of the strap attachable to and detachable from the second strap connection provided on the support plate at a distal portion thereof so that either or both the first section and the second section of the strap are removably attachable to and detachable from their respective first and second strap connections to capture the body organ between the manipulator and the strap.

3. The medical device of claim 1 wherein the manipulator comprises a drive rod detachably connected to a support plate, and wherein the drive rod is manipulatable from the remote location to move the strap along the inside passage of the conduit with the first section of the strap removably attachable to the first strap connection provided on either the drive rod or the support plate adjacent to their connection and wherein the second section of the strap is removably attachable to the second strap connection provided on the support plate at a distal portion thereof so that either or both of the first section and the second section of the strap are removably attachable to their respective first and second strap connections to capture the body organ between the support plate and the strap.

4. The medical device of claim 1 wherein the strap has a longitudinal axis and further comprising a guide provided on the conduit for holding and directing movement of the manipulator along and through the conduit while preventing the manipulator from rotating about the longitudinal axis thereof relative to the inside passage of the conduit.

5. The medical device of claim 1 wherein a lock is provided on the conduit, the lock being accessible from the remote location and being movable to an enabled position to prevent movement of the manipulator along and through the conduit and wherein the lock is movable to a disabled position to enable movement of the manipulator along the inside passage of the conduit.

6. The medical device of claim 1 including a seal inside the conduit that seals between the conduit and the manipulator to prevent fluids present inside the body cavity from moving through the conduit and past the seal when the distal portion of the conduit is inserted into the body cavity, the seal allowing movement of the manipulator along the inside passage of the conduit.

7. A method for holding and manipulating a body organ from a remote location outside a body cavity during a surgical procedure, which comprises:

a) providing a medical device that is insertable into the body cavity and which comprises an elongated conduit having a surrounding sidewall providing an inside passage extending to proximal and distal portions having respective spaced apart open ends, wherein the proximal portion of the conduit provides a handle for inserting the distal portion into the body cavity and for manipulating the distal portion from the remote location; a flexible strap having a width and a thickness so as to be received in a movable relationship in the inside passage of the conduit, wherein the strap has a first section and a second section; and a manipulator operatively associated with the strap and manipulatable from the remote location to move the strap along the inside passage of the conduit with the first section of the strap having a first attachment attachable to a first strap connection provided on the manipulator at an intermediate position located between proximal and distal portions thereof and wherein a second attachment provided on the strap at the second strap section is attachable to and detachable from a second strap connection provided at a distal end of the manipulator to thereby define an enclosure adjacent to the distal open end of the conduit;

b) inserting the medical device into the body cavity with the distal portion of the conduit positioned adjacent to the body organ and with the proximal portion of the conduit providing the handle positioned at the remote location;

c) manipulating the manipulator to deploy the strap out through the distal open end of the conduct;

d) grasping ahold of at least either the first section or the second section of the strap with a grasper introduced into the body cavity separate from the medical device to remove either the first or the second attachments from their respective connections to open the enclosure;

e) manipulating the opened strap around the body organ and then reattaching the first or the second attachment to its connection using the grasper to close the strap comprising the enclosure about the body organ;

f) manipulating the manipulator to tighten the enclosure about the body organ; and g) manipulating the handle to move the body organ inside the cavity as needed during the surgery.

8. The method of claim 7 wherein the manipulator comprises a drive rod and a support plate with the drive rod having a proximal portion positioned adjacent to the proximal portion of the conduit and a distal portion detachably connected to the support plate, and wherein the first section of the strap is removably attachable to the first strap connection provided on the drive rod at the intermediate position located between the proximal and distal portions of the manipulator, and with the second section of the strap attachable to and detachable from the second strap connection provided on the support plate at a distal portion thereof and including the step of removably attaching either or both of the first section and the second section of the strap to their respective first and second strap connections to capture the body organ between the manipulator and the strap.

9. The method of claim 7 wherein the manipulator comprises a drive rod connected to a support plate, and wherein the drive rod is manipulatable from the remote location to move the strap along the inside passage of the conduit with the first section of the strap removably attachable to the first strap connection provided on either the drive rod or the support plate adjacent to their connection and wherein the second section of the strap is removably attachable to a second strap connection provided on the support plate at a distal portion thereof and including the step of removably attaching either or both of the first section and the second section of the strap to their respective first and second strap connections to capture the body organ between the support plate and the strap.

* * * * *